(12) United States Patent
Chen et al.

(10) Patent No.: US 10,895,569 B2
(45) Date of Patent: Jan. 19, 2021

(54) GENOME-SCALE T CELL ACTIVITY ARRAY AND METHODS OF USE THEREOF

(71) Applicant: Yale University, New Haven, CT (US)

(72) Inventors: Lieping Chen, Hamden, CT (US); Jun Wang, New Haven, CT (US)

(73) Assignee: Yale University, New Haven, CT (US)

( * ) Notice: Subject to any disclaimer, the term of this patent is extended or adjusted under 35 U.S.C. 154(b) by 96 days.

(21) Appl. No.: 15/767,673

(22) PCT Filed: Oct. 11, 2016

(86) PCT No.: PCT/US2016/056395
§ 371 (c)(1),
(2) Date: Apr. 12, 2018

(87) PCT Pub. No.: WO2017/066172
PCT Pub. Date: Apr. 20, 2017

(65) Prior Publication Data
US 2018/0306778 A1    Oct. 25, 2018

Related U.S. Application Data

(60) Provisional application No. 62/241,466, filed on Oct. 14, 2015.

(51) Int. Cl.
*C04B 40/02* (2006.01)
*G01N 33/50* (2006.01)
*C40B 40/02* (2006.01)
*B01L 3/00* (2006.01)

(52) U.S. Cl.
CPC ....... *G01N 33/505* (2013.01); *G01N 33/5023* (2013.01); *B01L 3/5085* (2013.01); *B01L 2300/0829* (2013.01); *C40B 40/02* (2013.01); *G01N 2333/70532* (2013.01)

(58) Field of Classification Search
None
See application file for complete search history.

(56) References Cited

U.S. PATENT DOCUMENTS

2003/0054354 A1    3/2003    Bennett et al.
2009/0252737 A1    10/2009   McIntire et al.

FOREIGN PATENT DOCUMENTS

TW    201514299 A    4/2015

OTHER PUBLICATIONS

Yao et al. (2012) The Journal of Immunology vol. 188 p. 178.19.*
Madan et al., Clinical evaluation of TRICOM vector therapeutic cancer vaccines. Semin Oncol. Jun. 2012;39(3):296-304.
Swallow et al., B7h, a novel costimulatory homolog of B7.1 and B7.2, is induced by TNFalpha. Immunity. Oct. 1999;11(4):423-32.
Tseng et al., B7-DC, a new dendritic cell molecule with potent costimulatory properties for T cells. J Exp Med. Apr. 2, 2011;193(7):839-45.
International Search Report and Written Opinion for Application No. PCT/US2016/056395, dated Mar. 14, 2017, 20 pages.

(Continued)

*Primary Examiner* — Christian C Boesen
(74) *Attorney, Agent, or Firm* — McCarter & English, LLP; Maria Laccotripe Zacharakis; Maneesh Gulati, Esq.

(57) ABSTRACT

The present invention provides Genome-Scale T Cell Activity Arrays (GS-TCAA), as well as methods of making these arrays and methods of using them to identify immune modulators.

19 Claims, 9 Drawing Sheets

(56) References Cited

OTHER PUBLICATIONS

Leitner et al., T cell stimulator cells, an efficient and versatile cellular system to assess the role of costimulatory igands in the activation of human T cells. J Immunol Methods. 2010;362(1-2):131-141.

Torgersen et al., A soluble LAT deletion mutant inhibits T-cell activation: reduced recruitment of signalling molecules to glycolipid-enriched microdomains. Cell Signal. 2001;13(3):213-220.

* cited by examiner

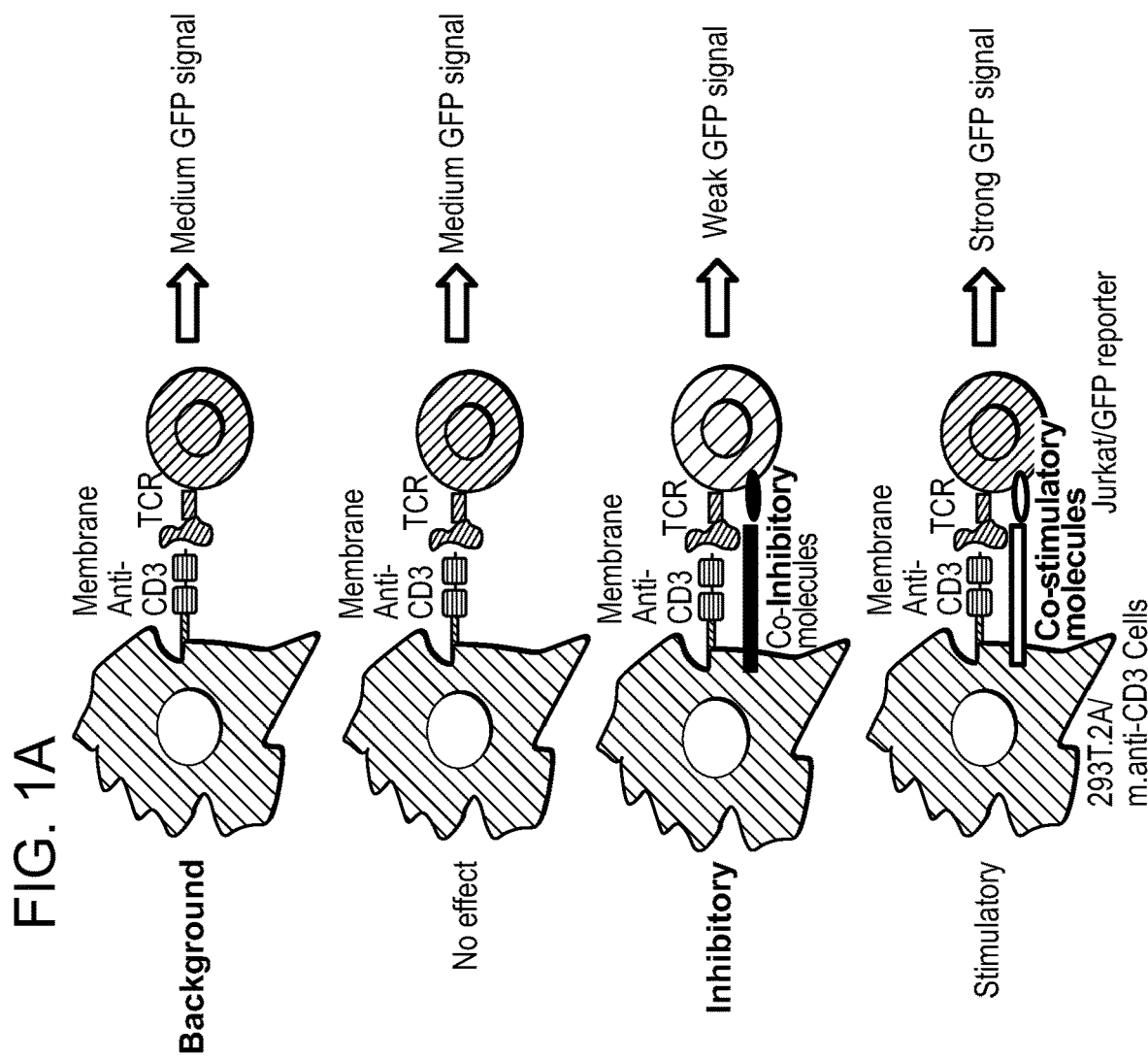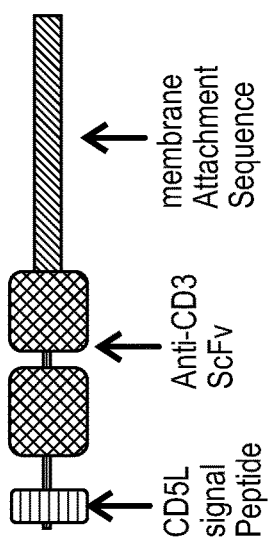

GENOME-SCALE T CELL ACTIVITY ARRAY AND METHODS OF USE THEREOF

RELATED APPLICATION

This application is a 35 U.S.C. § 371 national stage filing of International Application No. PCT/US2016/056395, filed on Oct. 11, 2016, which claims the benefit of priority to U.S. Provisional Patent Application No. 62/241,466, filed on Oct. 14, 2015. The entire contents of each of the foregoing applications are incorporated herein by reference.

BACKGROUND OF INVENTION

Co-signaling surface receptor-ligand pathways are essential for T cell activation and inhibition which tightly regulate T cell biological networks. In the last decade, this field has witnessed the development of immunomodulatory therapy approaches that target co-signaling molecules and pathways and combat many diseases, including autoimmune diseases and various cancers. The recent success of clinical trials and FDA regulatory approval of antibodies targeting the PD-1/B7-H1 (PD-L1) pathway, have provided unprecedented clinical responses with minimal adverse effects in a wide spectrum of advanced human cancers (Brahmer, J R et al., *N Engl J Med* 366(26): 2455-2465, 2012; Topalian, S L et al., *N Engl J Med* 366(26): 2443-2454, 2012). This type of treatment is superior to other therapies in terms of efficacy, toxicity, and durability and represents the benefits of tumor-site T cell immune modulatory strategies for cancer treatment (Sznol M and Chen L, *Clin Cancer Res* 19(5): 1021-1034, 2013). However, despite the exciting responses, a large portion of cancer patients do not respond to anti-PD-1 therapy. Therefore, there is a strong need to determine what other factors are involved in primary and acquired immune resistance (Sznol M and Chen L, *Clin Cancer Res* 19(5): 1021-1034, 2013) and what additional mechanisms are responsible for immune-evasion besides the PD-1/B7-H1 pathway. A comprehensive understanding of how human cell surface molecules regulate T cell responses will assist in identifying novel immune modulators and represents an important direction for the development of new immuno-therapeutic agents.

Membrane proteins play critical roles in the functioning of cells. Communication is one of the most important roles, where the cell surface proteins act as a receptor and are capable of either transducing signals between cells or mediating interaction between the internal and external environments. In addition to serving as a way for the cell to gather information and to relay signals, membrane proteins can also function as transporters and are associated with controlling the exchange of materials across the cell membrane. Membrane proteins are of particular interest as a target for therapeutic agents as they are more accessible. However, little is known about the immune function of most human membrane proteins, and there is no well-established system to assay T cell activity at the genome level. Therefore, there exists an ongoing and unmet need for compositions and methods that are capable of identifying novel immune-regulatory membrane proteins with drug potential in order to broaden the success rate and take full advantage of anti-tumor and autoimmune immunotherapies.

SUMMARY OF THE INVENTION

The present invention is based, at least in part, on the development of a novel genome-scale T cell activity array (GS-TCAA) which permits the identification of human membrane proteins that are involved in regulating T cell biological networks. The GS-TCAA allows for the study of different T cell activities such as proliferation, suppression, and exhaustion in more than 90% of all human membrane genes using a new cell-based fluorescent reporter system. This approach provides a comprehensive understanding of how human cell-surface molecules regulate T cell responses and assists in the identification of novel immune modulators. With the GS-TCAA, treatments can be targeted, identified, and developed by identifying unknown co-signaling molecules and pathways that are present in autoimmune diseases and cancers.

Accordingly, in one aspect, the invention includes a Genome-Scale T Cell Activity Array (GS-TCAA), comprising a solid support structure comprising a plurality of wells wherein each of the plurality of wells comprises: a first cell that expresses a membrane associated anti-CD3 antibody, or antigen-binding fragment thereof, wherein the first cell has been transfected with a cDNA library encoding a plurality of human membrane genes in a manner that allows the display on the first cell of a protein encoded by one of the plurality of human membrane genes; a second cell that expresses a receptor on the cell surface and a reporter gene; wherein interaction between the receptor and the anti-CD3 antibody, or antigen-binding fragment thereof, provides a primary signal and stimulates the activity of the second cell line, and wherein an increase in the expression level of the reporter gene indicates that the displayed protein encoded by one of the plurality of human membrane genes acts as a stimulatory co-signaling molecule and stimulates the activity of the second cell line, and wherein a decrease in the expression level of the reporter gene indicates that the displayed protein encoded by one of the plurality of human membrane genes acts as an inhibitory co-signaling molecule and inhibits the activity of the second cell line.

In some embodiments, the solid support structure is a multi-well plate. In other embodiments, the multi-well plate is selected from the group consisting of a 96-well plate, a 384-well plate and a 1536-well plate.

In some embodiments, the first cell is a human 293T cell. In other embodiments, the first cell is a human 293T.2A cell which expresses an immune-related adaptor. In some embodiments, the immune-related adaptor is selected from the group consisting of DAP10, DAP12, FcRγ and CD3E.

In some embodiments, the second cell is an immune cell. In other embodiments, the immune cell is a myeloid-derived suppressor cell (MDSC). In some embodiments, the immune cell is a T cell. In some embodiments, the T cell is selected from the group consisting of a Jurkat cell, a naïve T cell, an effector T cell, an exhausted T cell, an anergic T cell and a regulatory T cell.

In some embodiments, the reporter gene is contained in a DNA construct selected from the group consisting of a cytotoxicity related reporter construct, an apoptosis related reporter construct and a proliferation related reporter construct. In other embodiments, the cytotoxicity related reporter construct is a fluorescence-based reporter construct. In some embodiments, the apoptosis related reporter construct is a fluorescence-based reporter construct. In some embodiments, the fluorescence-based reporter construct contains a T cell related transcription responsive element followed by a minimal CMV promoter and a GFP reporter gene. In other embodiments, the T cell related transcription response element is selected from the group consisting of NF-kb, NF-AT, AP-1, EGR2, MAPK and PI3K. In some embodiments, the reporter gene in the proliferation related reporter construct is a cytokine gene. In some embodiments, the cytokine is selected from the group consisting of IFN-gamma, TNF-alpha and IL-10.

In some embodiments, the plurality of human membrane genes comprises a gene selected from a receptor gene, an immunoglobulin gene, a transporter gene and a signaling gene. In some embodiments, the plurality of human membrane genes comprises about 1,000-7,000 genes. In other embodiments, the plurality of human membrane genes comprises about 2,000-5,000 genes. In yet another embodiment, the plurality of human membrane genes comprises about 4,000-7,000 genes.

In some embodiments, the activity of the second cell is selected from the group consisting of cell proliferation, cell suppression, cell exhaustion, cell apoptosis, and cytokine release from cells.

In one aspect, the invention includes a method of making a Genome-Scale T cell Activity Array (GS-TCAA), the method comprising: providing a solid support structure comprising a plurality of wells; culturing a first cell that expresses a membrane associated anti-CD3 antibody, or antigen-binding fragment thereof, into each of the plurality of wells; transfecting the first cell with a cDNA library encoding a plurality of human membrane genes in a manner that allows the display on the first cell of a protein encoded by one of the plurality of human membrane genes; and co-culturing a second cell that expresses a receptor on the cell surface and a reporter gene into each of the plurality of wells, thereby preparing a Genome-Scale T cell Activity Array, wherein interaction between the receptor and the anti-CD3 antibody, or antigen-binding fragment thereof, provides a primary signal and stimulates the activity of the second cell line, and wherein an increase in the expression level of the reporter gene indicates that the displayed protein encoded by one of the plurality of human membrane genes acts as a stimulatory co-signaling molecule and stimulates the activity of the second cell line, and wherein a decrease in the expression level of the reporter gene indicates that the displayed protein encoded by one of the plurality of human membrane genes acts as an inhibitory co-signaling molecule and inhibits the activity of the second cell line.

In some embodiments, the solid support structure is a multi-well plate. In some embodiments, the multi-well plate is selected from a group consisting of a 96-well plate, a 384-well plate and a 1536-well plate.

In some embodiments, the first cell is a human 293T cell. In other embodiments, the first cell is a human 293T.2A cell that expresses an immune-related adaptor. In some embodiments, the immune-related adaptor is selected from the group consisting of DAP10, DAP12, FcRγ and CD3E.

In some embodiments, the second cell is an immune cell. In other embodiments, the immune cell is a myeloid-derived suppressor cell (MDSC). In some embodiments, the immune cell is a T cell. In some embodiments, the T cell is selected from the group consisting of a Jurkat cell, a naïve T cell, an effector T cell, an exhausted T cell, an anergic T cell and a regulatory T cell.

In some embodiments, the reporter gene is contained in a DNA construct selected from the group consisting of a cytotoxicity related reporter construct, an apoptosis related reporter construct and a proliferation related reporter construct. In other embodiments, the cytotoxicity related reporter construct is a fluorescence-based reporter construct. In some embodiments, the apoptosis related reporter construct is a fluorescence-based reporter construct. In some embodiments, the fluorescence-based reporter construct contains a T cell related transcription responsive element followed by a minimal CMV promoter and a GFP reporter gene. In other embodiments, the T cell related transcription response element is selected from the group consisting of NF-kb, NF-AT, AP-1, EGR2, MAPK and PI3K. In some embodiments, the reporter gene in the proliferation related reporter construct is a cytokine gene. In some embodiments, the cytokine is selected from the group consisting of IFN-gamma, TNF-alpha and IL-10.

In some embodiments, the plurality of human membrane genes comprises a gene selected from a receptor gene, an immunoglobulin gene, a transporter gene and a signaling gene. In some embodiments, the plurality of human membrane genes comprises about 1,000-7,000 genes. In other embodiments, the plurality of human membrane genes comprises about 2,000-5,000 genes. In yet another embodiment, the plurality of human membrane genes comprises about 4,000-7,000 genes.

In some embodiments, the activity of the second cell is selected from the group consisting of cell proliferation, cell suppression, cell exhaustion, cell apoptosis, and cytokine release from cells.

One aspect of the invention provides a method of identifying an immune modulator, the method comprising: providing the Genome-Scale T cell Activity Array (GS-TCAA) as described herein; allowing the expression of one of the plurality of human membrane genes in the first cell, co-culturing the first cell and the second cell; detecting the expression level of the reporter gene in the second cell; and comparing the expression level of the reporter gene with the expression level of the reporter gene in a control second cell wherein the control second cell is co-cultured with a control first cell that has not been transfected with one of the plurality of human membrane genes, wherein an increase in the expression level of the reporter gene indicates that the displayed protein encoded by one of the plurality of human membrane genes acts as a stimulatory co-signaling molecule and stimulates the activity of the second cell line, and wherein a decrease in the expression level of the reporter gene indicates that the displayed protein encoded by one of the plurality of human membrane genes acts as an inhibitory co-signaling molecule and inhibits the activity of the second cell line, thereby identifying the immune modulator.

In some embodiments, the immune modulator is selected from the group consisting of FOLH1, FAS, IL3RA, CD248, THBD, B7.1, GJB1, OX40L, 4-1BBL and B7.2. In other embodiments, the immune modulator is selected from the group consisting of FLT1, CXCR6, SEMA6a, RHCE, FCRLA, TNFRSF19, SEC22b, B3GNT1, NFAM1. LY6 and GP1BA. In some embodiments, the immune modulator is selected from the group consisting of FLT1, SEMA6a, SEC22b and GP1BA.

In some embodiments, the method is automated. In other embodiments, the method is performed using robotics. In some embodiment, the method is performed using a robotic liquid handling technique. In other embodiments, the method is performed using an automated plate handling system.

In some embodiments, the method further comprises performing an assay selected from the group consisting of an in vitro functional assay, an in vivo assay, a receptor array assay, a bioinformatics assay, or a combination thereof.

In some embodiments, the in vitro functional assay comprises culturing the second cell expressing one of the plurality of human membrane genes and the membrane-associated anti-CD3 antibody, or antigen-binding fragment thereof, with a primary T cell; and performing an in vitro functional assay selected from the group consisting of a proliferation assay, an apoptosis assay and a cytokine release assay. In some embodiments, the primary T cell is a human primary CD8 cell and/or a human primary CD4 cell.

In some embodiments, the receptor array assay is performed to identify interacting proteins of the immune modulator. In other embodiments, the receptor array comprises: a solid support structure comprising a plurality of wells wherein each of the plurality of wells comprises: a cell that has been transfected with a cDNA library encoding a plurality of receptor genes in a manner that allows the display on the cell of a receptor encoded by one of the plurality of receptor genes; a recombinant protein comprising an immune modulator fused with a tag; a fluorescently labeled antibody specific for the tag; wherein a detectable fluorescence signal is an indication that the immune modulator interacts with the receptor.

In some embodiments, the tag is selected from the group consisting of a mouse IgG2a Fc tag, a human IgG1 Fc tag, a FLAG tag and a 6× His tag. In some embodiments, the immune modulator is a full length protein of the immune modulator. In other embodiments, the immune modulator is the extracellular domain of the immune modulator.

In some embodiments, the in vivo assay comprises administering the immune modulator to an animal model for an autoimmune disease or cancer. In some embodiments, the animal model is a NOD-scid IL2Rgamma$^{null}$ mouse model injected with human melanoma cells and tumor-reactive T cells. In other embodiments, the animal model is a humanized mouse model. In yet another embodiment, the humanized mouse model is an immune-patient-derived xenograft (immune-PDX) model.

One aspect of the invention provides a method of treating an autoimmune disease or cancer in a subject in need thereof, comprising administering to the subject an effective amount of an immune modulator identified by the method as described herein, thereby treating an autoimmune disease or cancer in the subject.

In some embodiments, the immune modulator is selected from the group consisting of FOLH1, FAS, IL3RA, CD248, THBD, B7.1, GJB1, OX40L, 4-1BBL and B7.2. In other embodiments, the immune modulator is selected from the group consisting of FLT1, CXCR6, SEMA6a, RHCE, FCRLA, TNFRSF19, SEC22b, B3GNT1, NFAM1. LY6 and GP1BA.

Another aspect of the invention features a method of treating an autoimmune disease or cancer in a subject in need thereof, comprising administering to the subject an effective amount of a regulator of an immune modulator identified by the method as described herein, thereby treating an autoimmune disease or cancer in the subject.

In some embodiments, the immune modulator is selected from the group consisting of FOLH1, FAS, IL3RA, CD248, THBD, B7.1, GJB1, OX40L, 4-1BBL and B7.2. In other embodiments, the immune modulator is selected from the group consisting of FLT1, CXCR6, SEMA6a, RHCE, FCRLA, TNFRSF19, SEC22b, B3GNT1, NFAM1. LY6 and GP1BA. In some embodiments, the regulator of an immune modulator increases the expression level and/or the activity level of the immune regulator. In other embodiments, the regulator of an immune modulator decreases the expression level and/or the activity level of the immune regulator.

The present invention is illustrated by the following drawings and detailed description, which do not limit the scope of the invention described in the claims.

BRIEF DESCRIPTION OF THE DRAWINGS

FIG. 1A graphically depicts the basic principle for the Genome-Scale T Cell Activity Array (GS-TCAA). Briefly, 293T.2A cells stably expressing membrane associated anti-human CD3 antibody ScFv (293T.2A/m.anti-CD3) stimulate T cell activation in Jurkat/reporter cells and generate detectable GFP signals. Transfection of individual membrane genes from the cDNA library potentially affects the outcome of T cell activities. If the molecule is not effective, the GFP signal will remain similar. If the molecule is stimulatory, a stronger GFP signal will be detected. If the molecule is inhibitory, a weaker GFP signal will be observed. FIG. 1B graphically depicts the membrane associated anti-human CD3 antibody ScFv construct, which contains the signal peptide sequence of the CD5L gene, and is flanked by anti-CD3 ScFv and membrane attachment sequences. FIG. 1C graphically depicts the GFP reporter construct which contains a T cell related transcription factor response element (TFRE) followed by a minimal CMV promoter and a GFP reporter gene.

DETAILED DESCRIPTION OF THE INVENTION

Figure 2B:
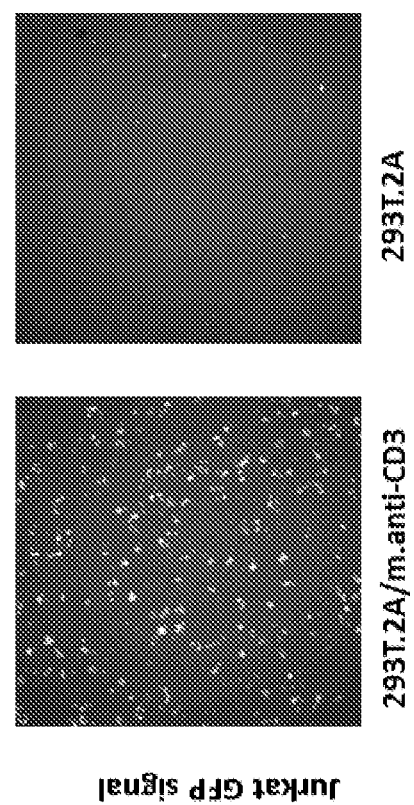
FIG. 2B is an image depicting that when 293T.2A cells with or without m.anti-CD3 plasmid transfection were co-cultured with Jurkat/NF-Kb GFP cells, the GFP signal was detected only in cells with m.anti-CD3 12 hours after co-culture. Data was obtained in 1536 imaging plates.

The present invention is based, at least in part, on the development of a novel genome-scale T cell activity array (GS-TCAA) which can be used to identify novel immune modulators, e.g., immune modulators, that regulate T cells. The GS-TCAA allows for the study of different T cell activities such as proliferation, suppression, and exhaustion in more than 90% of all human membrane genes using a new cell-based fluorescent reporter system. This approach provides a comprehensive understanding of how human cell-surface molecules regulate T cell responses and assists in the identification of novel immune modulators. With the GS-TCAA, treatments can be targeted, identified, and developed by identifying unknown co-signaling molecules and pathways that are present in autoimmune diseases and cancers.

Thus, the invention provides, in one embodiment, a genome-scale T cell activity array (GS-TCAA), as well as methods for making a genome-scale T cell activity array (GS-TCAA). Another embodiment of the invention includes methods relating to identifying immune modulators using the genome-scale T cell activity array (GS-TCAA). In a further embodiment, the invention includes methods and compositions for treating an autoimmune disease or cancer by administering to a subject an immune modulator and/or a regulator of an immune modulator.

I. Definitions

In order that the present invention may be more readily understood, certain term are first defined.

Unless otherwise defined herein, scientific and technical terms used in connection with the present invention shall have the meanings that are commonly understood by those of ordinary skill in the art. The meaning and scope of the terms should be clear, however, in the event of any latent ambiguity, definitions provided herein take precedent over any dictionary or extrinsic definition.

The use of the terms "a" and "an" and "the" and similar referents in the context of describing the invention (especially in the context of the following claims) are to be construed to cover both the singular and the plural (i.e., one or more), unless otherwise indicated herein or clearly contradicted by context. The terms "comprising, "having," "including," and "containing" are to be construed as open-ended terms (i.e., meaning "including, but not limited to") unless otherwise noted. Recitation of ranges of values herein are merely intended to serve as a shorthand method of referring individually to each separate value recited or falling within the range, unless otherwise indicated herein, and each separate value is incorporated into the specification as if it were individually recited. Ranges provided herein are understood to be shorthand for all of the values within the range. For example, a range of 1 to 50 is understood to include any number, combination of numbers, from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 or sub-ranges from the group consisting of 10-40, 20-50, 5-35, etc.

As described herein, the term "well" generally refers to a bounded area within a container, which may be either discrete (e.g., to provide for an isolated sample) or in communication with one or more other bounded areas (e.g., to provide for fluid communication between one or more samples in a well). For example, cells grown on a substrate are normally contained within a well that may also contain culture medium for living cells. Substrates can comprise any suitable material, such as plastic, glass, and the like. Plastic is conventionally used for maintenance and/or growth of cells in vitro.

A "multi-well plate" is an example of a substrate comprising more than one well in an array. Multi-well plates useful in the invention can be of any of a variety of standard formats (e.g., plates having 2, 4, 6, 24, 96, 384, or 1536, etc., wells), but can also be in a non-standard format as described in further detail below.

As used herein, the term "cell" includes prokaryotic and eukaryotic cells. In one embodiment, a cell suitable for use in the arrays and the methods of the invention is a bacterial cell. In another embodiment, a cell suitable for use in the arrays and the methods of the invention is a fungal cell, such as a yeast cell. In another embodiment, a cell suitable for use in the arrays and the methods of the invention is a vertebrate cell, e.g., an avian or mammalian cell. In a preferred embodiment, a cell suitable for use in the arrays and the methods of the invention is a mammalian cell.

As used herein, the term "immune cell" includes cells that are of hematopoietic origin and that play a role in the immune response. Immune cells include cells of the innate immune system and cells of the adaptive immune system. Immune cells include, for example, lymphocytes, such as B cells and T cells; natural killer cells; and myeloid cells, such as monocytes, macrophages, eosinophils, mast cells, basophils, and granulocytes.

In one embodiment, an immune cell is a cell of the innate immune system. The "innate immune system" is the non-specific immune system that controls the body's response to an agent until the more specific adaptive immune system can produce specific antibodies and/or T cells (Modlin et al., *N. Engl. J. Med* 1999, 340:1834-1835). The innate immune system generally involves phagocytic cells (e.g., neutrophils, monocytes, and macrophages); cells that release inflammatory mediators (e.g., basophils, mast cells, and eosinophils); natural killer cells (NK cells); and dendritic cells (DCs). In contrast, the "adaptive", or "acquired, immune system", is very specific in its responses. It is called an adaptive system because is occurs during the lifetime of an individual as an adaptation to infection with a pathogen. Adaptive immunity can be artificially acquired in response to a vaccine (antigens) or by administering antibodies, or can be naturally acquired by infection.

As used herein, "antigen presenting cell" refers to cells that display foreign antigens complexed with major histocompatibility complexes (MHCs) on their surfaces, which are then recognized by T cells using their T cell receptors. Antigen presenting cells include cells that constitutively express MHC molecules (e.g., B lymphocytes, monocytes, dendritic cells, and Langerhans cells) as well as other antigen presenting cells that do not constitutively express MHC molecules (e.g., keratinocytes, endothelial cells, astrocytes, fibroblasts, and oligodendrocytes).

As used herein, the term "T cell" (i.e., T lymphocyte) is intended to include all cells within the T cell lineage, including thymocytes, immature T cells, mature T cells and the like, from a mammal (e.g., human). T cells include mature T cells that express either CD4 or CD8, but not both, and a T cell receptor. The various T cell populations described herein can be defined based on their cytokine profiles and their function.

As used herein, the term "naïve T cells" includes T cells that have not been exposed to cognate antigen and so are not activated or memory cells. Naïve T cells are not cycling and human naïve T cells are CD45RA+. If naïve T cells recognize antigen and receive additional signals depending upon but not limited to the amount of antigen, route of administration and timing of administration, they may proliferate and differentiate into various subsets of T cells, e.g., effector T cells.

As used herein, the term "effector T cell" includes T cells which function to eliminate antigen (e.g., by producing cytokines which modulate the activation of other cells or by cytotoxic activity). The term "effector T cell" includes T helper cells (e.g., Th1 and Th2 cells) and cytotoxic T cells. Th1 cells mediate delayed type hypersensitivity responses and macrophage activation while Th2 cells provide help to B cells and are critical in the allergic response (Mosmann and Coffman, 1989, *Annu. Rev. Immunol.* 7, 145-173; Paul and Seder, 1994, *Cell* 76, 241-251; Arthur and Mason, 1986, *J. Exp. Med.* 163, 774-786; Paliard et al., 1988, *J. Immunol.* 141, 849-855; Finkelman et al., 1988, *J. Immunol.* 141, 2335-2341).

As used herein, the term "regulatory T cell" includes T cells which produce low levels of IL-2, IL-4, IL-5, and IL-12. Regulatory T cells produce TNFα, TGFβ, IFN-γ, and IL-10, albeit at lower levels than effector T cells. Although TGFβ is the predominant cytokine produced by regulatory T cells, the cytokine is produced at lower levels than in Th1 or Th2 cells, e.g., an order of magnitude less than in Th1 or Th2 cells. Regulatory T cells can be found in the CD4+CD25+ population of cells (see, e.g., Waldmann and Cobbold. 2001. *Immunity.* 14:399). Regulatory T cells actively suppress the proliferation and cytokine production of Th1, Th2, or naïve T cells which have been stimulated in culture with an activating signal (e.g., antigen and antigen presenting cells or with a signal that mimics antigen in the context of MHC, e.g., anti-CD3 antibody plus anti-CD28 antibody).

As used herein, the term "exhausted T cell" refers to malfunctional T cells that are characterized by the stepwise and progressive loss of T-cell functions and can culminate in the physical deletion of the responding cells. Exhausted T cell may arise during chronic infections and cancer. For example, exhaustion is well-defined during chronic lymphocytic choriomeningitis virus infection and commonly develops under conditions of antigen-persistence, which occur following many chronic infections that are of significant public health concern including hepatitis B virus, hepatitis C virus and human immunodeficiency virus infections, as well as during tumor outgrowth (see. e.g., John Wherry, *Nature Immunology* 12, 492-499, 2011).

As used herein, the term "anergic T cell" refers to T cells that are functionally inactivated and unable to initiate a productive response even when antigen is encountered in the presence of full co-stimulation (see, e.g., Macián F. et al, *Curr Opin Immunol.* 2004, 16(2):209-16.) T cell anergy is a tolerance mechanism in which the lymphocyte is intrinsically functionally inactivated following an antigen encounter, but remains alive for an extended period of time in a hyporesponsive state. Models of T cell anergy affecting both CD4+ and CD8+ cells fall into two broad categories. One, clonal anergy, is principally a growth arrest state, whereas the other, adaptive tolerance or in vivo anergy, represents a more generalized inhibition of proliferation and effector functions (see, e.g., Schwartz R H. *Annu Rev Immunol.* 2003; 21:305-34).

As used herein, the term "immune modulator" refers to any molecules identified using the GS-TCAAs that can regulate the immune system. For example, the immune modulators identified by the arrays and methods of the present invention are molecules that regulate T cell activity. For example, the immune modulator may increase the T cell activity or may decrease T cell activity. The immune modulators may be used to treat autoimmune diseases and/or cancer.

As used herein, the term "regulator of an immune modulator" refers to any agent that can regulate the expression and/or activity of an immune modulator as described above. The regulator of an immune modulator can increase or decrease the expression and/or activity of the immune modulator. In one embodiment, the regulator of an immune modulator acts directly on the immune modulator, e.g., it is an antibody which binds to the immune modulator and either activates or inhibits its function. The regulator of the immune modulator may also be used to treat autoimmune diseases and/or cancer.

The term "culturing" refers to the in vitro propagation of cells or organisms on or in media of various kinds. It is understood that the descendants of a cell grown in culture may not be completely identical (i.e., morphologically, genetically, or phenotypically) to the parent cell.

The term "interact" as used herein is meant to include detectable interactions between molecules, such as can be detected using, for example, a fluorescence based detection method, a yeast two hybrid assay, chromatin immunoprecipitation, or co-immunoprecipitation. The term "interact" is also meant to include "binding" interactions between molecules. Interactions may be protein-protein or protein-nucleic acid in nature.

The term "transfection" is used herein to mean the delivery of nucleic acid, protein or other macromolecule to a target cell, such that the nucleic acid, protein or other macromolecule is expressed or has a biological function in the cell.

The term "fluorescent" refers to any substance or agent that is capable of exhibiting "fluorescence" (or "photoluminescence"), which is the emission of light triggered by the molecular absorption of a photon with shorter wavelength. Fluorescence thus is dependent on an "excitation light source" that is distinct from the longer wavelength fluorescence "emission" emanating from the fluorophore. Detection of fluorescence emission requires that a detector that responds only to the emission light and not to the excitation light.

II. Genome-Scale T Cell Activity Array (GS-TCAA)

In one aspect, the present invention features a genome-scale T cell activity array (GS-TCAA). The array of the invention comprises a solid support structure comprising a plurality of wells wherein each of the plurality of wells comprises a first cell and a second cell. The first cell expresses a membrane associated anti-CD3 antibody, or antigen-binding fragment thereof, and has also been transfected with a cDNA library encoding a plurality of human membrane genes in a manner that allows the display on the first cell of a protein encoded by one of the plurality of human membrane genes. The second cell expresses a receptor on the cell surface which interacts with the anti-CD3 antibody, or antigen-binding fragment thereof, presented on the first cell, and provides a primary signal to stimulate the activity of the second cell. In addition, the second cell expresses a reporter gene, wherein an increase in the expression level of the reporter gene indicates that the displayed protein encoded by one of the plurality of human membrane genes being transfected into the first cell acts as a stimulatory co-signaling molecule and stimulates the activity of the second cell line, and wherein a decrease in the expression level of the reporter gene indicates that the displayed protein encoded by one of the plurality of human membrane genes acts as an inhibitory co-signaling molecule and inhibits the activity of the second cell line.

The solid support structure used in the present invention may be any support suitable for holding, and enabling the growth of, cultured cells. Suitable materials to be used as a solid support include but are not limited to plastic, glass, polymer, metal and the like. In one embodiment, the solid support is a multi-well plate. Multi-well plates useful in the invention can be of any of a variety of standard formats, for example, a 4-well plate, a 6-well plate, 24-well plate, 96-well plate, a 384-well plate and a 1536-well plate. Alternatively, the multi-well plates used in the present invention can be a non-standard format, for example, plates having at least 500, at least 1000, at least 1500 or at least 2000 wells.

Cells suitable for use in the arrays of the present invention include all types of eukaryotic and prokaryotic cells. In preferred embodiments, the cells are eukaryotic cells, in particular, mammalian cells. In certain embodiments, a cell used in the arrays of the present invention is a genetically engineered cell, such as a cell that has been transformed with at least one heterologous nucleic acid sequence. Such a nucleic acid molecule can encode a T cell receptor, or any human membrane protein. A genetically engineered cell can include more than one heterologous nucleic acid sequence. A nucleic acid sequence, or molecule, as described herein can be DNA, RNA, or hybrids or derivatives of either DNA or RNA. Nucleic acid molecules for use in the arrays of the invention can include regulatory regions that control expression of the nucleic acid molecule (e.g., transcription or translation control regions), full-length or partial coding regions, and combinations thereof. It is to be understood that any portion of a nucleic acid molecule can be produced by: (1) isolating the molecule from its natural milieu; (2) using recombinant DNA technology (e.g., PCR amplification, cloning); or (3) using chemical synthesis methods. A gene includes all nucleic acid sequences related to, for example, a natural cell surface receptor gene such as regulatory regions that control production of a cell surface receptor encoded by that gene (such as, but not limited to, transcription, translation or post-translation control regions) as well as the coding region itself.

A nucleic acid molecule can include functional equivalents of natural nucleic acid molecules encoding a protein or functional equivalents of natural nucleic acid sequences capable of being bound by proteins. Functional equivalents of natural nucleic acid molecules can include, but are not limited to, natural allelic variants and modified nucleic acid molecules in which nucleotides have been inserted, deleted, substituted, and/or inverted in such molecules without adversely affecting the function of products encoded by such sequences. In some embodiments, the nucleic acid encodes a human membrane protein. In some embodiments, the nucleic acid is a reporter gene.

Transformation of a heterologous nucleic acid molecule (e.g., a heterologous cell surface receptor encoding nucleic acid molecule) into a cell suitable for use in the arrays of the present invention can be accomplished by any method by which a gene may be inserted into a cell. Transformation techniques include, but are not limited to, transfection, retroviral infection, electroporation, lipofection, bacterial transfer and spheroplast fusion. Nucleic acid molecules transformed into cells suitable for use in the arrays of the present invention can either remain on extra-chromosomal vectors (transient transfection) or can be integrated into the cell genome (stable transfection). In order to generate a stable cell line, a gene of interest and a suitable viral transcription promoter is inserted into a suitable vector such as a plasmid or a retrovirus, containing a selectable marker that confers resistance to growth suppressing compounds, such as antibiotics, e.g., neomycin. The DNA construct is introduced into cells and is stably integrated into the genome of the host cell line to provide a stable cell line which may be selectively cultured in the presence of an appropriate antibiotic to which the engineered cell is resistant. Alternatively, transient transduction of host cells may suitably be performed using adenoviral vectors. The vector DNA molecule does not integrate into the host chromatin but exists as an extrachromosomal molecule with a lifetime of typically 24-96 hours, dependent on the cell type.

Expression of a nucleic acid molecule of the present invention in a cell can be accomplished using techniques known to those skilled in the art. Briefly, the nucleic acid molecule is inserted into an expression vector in such a manner that the nucleic acid molecule is operatively joined to a transcription control sequence in order to be capable of effecting either constitutive or regulated expression of the gene when the gene is transformed into a host cell. The phrase "recombinant molecule", as used herein refers to a gene operatively linked to at least one transcription control sequence on an expression vector. The phrase "expression vector", as used herein refers to a DNA or RNA vector that is capable of transforming a host cell, of replicating within the host cell, and of affecting expression of the operatively linked gene. Expression vectors are capable of replicating to either a high or low copy number depending on their inherent characteristics. Transcription control sequences, which can control the amount of protein produced, include sequences that control the initiation, elongation, and termination of transcription. Particularly important transcription control sequences are those which control transcription initiation, such as promoter and upstream activation sequences.

An expression system can be constructed from any of the known control elements operatively linked to nucleic acid sequences using methods known to those of skill in the art. See, for example, Sambrook et al., 1989, Molecular Cloning: A Laboratory Manual, Cold Spring Harbor Labs Press, which is incorporated by reference herein in its entirety.

In a preferred embodiment, the plurality of human membrane genes are transfected in the first cell in a manner that allows these genes to be expressed and individually displayed on the cell surface. To achieve this, the optimized reverse transfection protocol described in the Examples section may be used. Alternatively, the expression and the individual display of the genes may be achieved by any known gene transfer technique including, but not limited to, retrovirus transduction, lentivirus transduction, lipofection and CRISPR.

The first cell in the solid support structure of the present invention can be any standard cell known in the art suitable for transfection and expression of a human membrane gene, for example, a human 293T cell. Alternatively, the first cell is a Chinese Hamster Ovary (CHO) cell. Another example of the first cell is a COS-7 cell. In preferred embodiments, the first cell is a human 293T.2A cell which expresses an immune-related adaptor. Examples of the immune-related adaptor include, but are not limited to DAP10, DAP12, FcRγ and CD3E. The second cell of the present invention is an immune cell whose activity is modulated upon interaction with proteins displayed on the first cell. In some embodiments, the second cell in the arrays of the invention is an immune cell, for example, a T cell. Exemplary T cells include but not limited to Jurkat cells, naïve T cells, effector T cells, exhausted T cells, anergic T cells and regulatory T cells. Alternatively, the second cell may be a myeloid-derived suppressor cell.

In some embodiments, the second cell in the arrays of the invention is engineered to stably express a cell assay sensor or detectable reporter, for example, a reporter gene expressing a fluorescent protein, or expressing an enzyme, so as to provide a cellular assay readout. In some embodiments, the reporter gene is contained in a construct comprising an inducible transcription control element driving the expression of the reporter gene. In some embodiments, the reporter construct is a cytotoxicity related reporter construct. In other embodiments, the reporter construct is an apoptosis related reporter construct. In yet another embodiments, the reporter construct is a proliferation related reporter construct.

Reporter gene technology is widely used to monitor the cellular events associated with signal transduction and gene expression. In the context of the present invention, the term reporter gene is used to refer to a gene that allows the detection of the effect of a human membrane gene on the activity of a cell, e.g., a T cell, with a readily measurable phenotype that can be distinguished easily over a background. A reporter gene construct is comprised of an inducible transcriptional control element driving the expression of the reporter gene, for example using a T cell related transcription responsive elements for expression of a green fluorescent protein (GFP). Exemplary T cell related transcription responsive elements include, but are not limited to, NF-kB, NF-AT, AP-1, EGR2, MAPK and PI3K. Suitable reporter genes for use in the arrays of the present invention include, but are not limited to, enzymes, fluorescent proteins, photo-proteins, fusion proteins and epitope tags. Examples of enzyme reporter genes include, but are not limited to, beta-galactosidase, alkaline phosphatase, beta-lactamase, luciferase and nitroreductase. Examples of fluorescent proteins include, but are not limited to, Aequorea victoria green fluorescent protein (GFP) and variants thereof (e.g., cyan fluorescent protein and yellow fluorescent protein). Suitable photo-proteins include, but are not limited to, aequorin. Alternatively, the reporter gene of the present invention is a cytokine gene. Exemplary cytokine genes include, but are not limited to, IFN-gamma, TNF-alpha and IL-10.

One example of a reporter gene assay that may be performed according to the present invention employs cells engineered by the introduction of a nucleic acid molecule comprising a nucleotide sequence encoding a fluorescent protein which may be derived from GFP or any variants thereof, such as EGFP, YFP, or BFP (Shaner, N. C, et al, *Nat. Methods*, 2005, 2(12), 905-9), the nucleic acid molecule being operably linked to and under the control of an expression control sequence, for example, a T cell related transcription responsive element including, but not limited to, NF-kB, NF-AT, AP-1, EGR2, MAPK and PI3K. The fluorescence emission of the GFP or functional GFP analogue is then monitored as a means of measuring the activity of the T cell. The method may be used to detect and compare the effect of a membrane gene transfected into the first cell on the overall activity of the second cell.

The arrays of the present invention also contain a cDNA library encoding a plurality of human membrane genes. Methods of generating a cDNA library are well known in the art. Briefly, in the classical method for constructing cDNA libraries, mRNA is first isolated from certain cells and is then treated with different enzymes and alkali in successive steps of the process. In parallel the vector (e.g., plasmid pBR322) is treated in such a way that insertion of the cDNA synthesized is possible. After annealing of cDNA and pre-treated vector, a suitable host (e.g., strain of *E. coli* K12) is transformed with the vector-cDNA constructs, plated on suitable substrates and incubated. All colonies from transformed cells obtained in this way constitute a cDNA library (Gubler et al, *Gene,* 25(2-3): 263-269, 1983). In some embodiments, the plurality of human membrane genes comprises about 1,000-7,000 genes, about 2,000-5,000 genes, about 4,000-7,000 genes or about 100-5,000 genes. For example, the plurality of human membrane genes comprises at least about 500, 1000, 2000, 3000, 4000, 5000, 6000 or 7000 human membrane genes. In some embodiments, the plurality of human membrane genes comprises more than 6,000 human membrane genes which covers more than 90% of all human membrane genes.

Membrane genes for use in the arrays of the present invention represent a full spectrum of the human membrane genome. In some embodiments, the membrane gene is a receptor gene. In other embodiments, the membrane gene is a signaling gene. In yet another embodiment, the membrane gene is an immunoglobulin gene. In some embodiments, the membrane gene is a transporter gene.

The arrays of the present invention allow screening for a variety of T cell activities including but not limited to, cell proliferation, suppression, exhaustion, cytotoxicity, apoptosis, and cytokine release, that occurs the T cell receptor on the T cell interacts with an antigen/MHC complex on the antigen-presenting cell or a signal that mimics antigen in the context of MHC, (e.g., anti-CD3 antibody). As used herein, "activation" of a T cell refers to induction of signal transduction pathways in the T cell resulting in T cell proliferation, T cell differentiation, and/or production of cellular products (e.g., cytokines).

According to the present invention, a T cell receptor (TCR), as described herein, specifically refers to the antigen receptor of a T cell. It is recognized in the art that there are a variety of other receptors expressed by a T cell which are important in T cell responses, including, but not limited to, CD3, CD4, CD8, CD28, CTLA-4, CD45, CD43 and Thy-1. A T cell receptor can be produced by expression of a naturally occurring gene encoding a T cell receptor and/or a heterologous nucleic acid molecule transformed into a cell. Similarly, a membrane protein as described herein can be produced in a cell by expression of a naturally occurring gene and/or by expression of a heterologous nucleic acid molecule transformed into the cell.

In the arrays of the present invention, the first cell (e.g., an human 293T.2A cell which serves as an antigen presenting cell) is cultured with the second cell (e.g., a T cell) under conditions (e.g., culture medium, temperature, oxygen, $CO_2$, incubation time) in which such cells can be maintained as viable cells and interact with other cells to activate signal transduction pathways. As such, the cells can be cultured in any suitable culture medium which contains components necessary for cell growth, such as carbon, nitrogen and micro-nutrients. Determination of suitable culture medium and growth conditions for such cells is well within the skill of the art.

III. Methods of Making a Genome-Scale T Cell Activity Array (GS-TCAA)

The present invention also provides methods of making a genome-scale T cell activity array (GS-TCAA). The methods include providing a solid support structure comprising a plurality of wells wherein each of the plurality of wells comprises a first cell and a second cell. The first cell is transfected to stably expresses a membrane associated anti-CD3 antibody, or antigen-binding fragment thereof. The second cell expresses a receptor on the cell surface which interacts with the anti-CD3 antibody, or antigen-binding fragment thereof, presented on the first cell and provides a primary signal to stimulate the activity of the second cell. The methods of the invention also involve culturing the first cell that expresses a membrane associated anti-CD3 antibody, or antigen-binding fragment thereof, into each of the plurality of wells; transfecting the first cell with a cDNA library encoding a plurality of human membrane genes in a manner that allows the display on the first cell of a protein encoded by one of the plurality of human membrane genes; and co-culturing into each of the plurality of wells with the second cell that expresses a receptor on the cell surface and a reporter gene. The second cell expresses a reporter gene, wherein an increase in the expression level of the reporter gene indicates that the displayed protein encoded by one of the plurality of human membrane genes being transfected into the first cell acts as a stimulatory co-signaling molecule and stimulates the activity of the second cell, and wherein a decrease in the expression level of the reporter gene indicates that the displayed protein encoded by one of the plurality of human membrane genes acts as an inhibitory co-signaling molecule and inhibits the activity of the second cell.

The solid support structure used in the methods of the present invention may be any support suitable for holding, and enabling the growth of, cultured cells, as described in above. In one embodiment, the solid support is a multi-well plate. Multi-well plates useful in the invention can be of any of a variety of standard formats, for example, a 4-well plate, a 6-well plate, 24-well plate, 96-well plate, a 384-well plate and a 1536-well plate. Alternatively, the multi-well plates used in the present invention can be a non-standard format, for example, plates having at least 500, at least 1000, at least 1500 or at least 2000 wells.

Cells suitable for use in the methods of the present invention include all types of eukaryotic and prokaryotic cells as described above. In preferred embodiments, the cells are eukaryotic cells, in particular, mammalian cells. In certain embodiments, a cell used in the methods of the present invention is a genetically engineered cell, such as a cell that has been transformed with at least one heterologous nucleic acid sequence. Such a nucleic acid molecule can encode a T cell receptor, a human membrane protein, or a reporter. Such nucleic molecule can be produced by any molecular biology techniques known in the art, or any methods as described above in Section II.

Transformation of such a heterologous nucleic acid molecule (e.g., a heterologous membrane protein encoding nucleic acid molecule) into a cell suitable for use in the methods of the present invention can be accomplished by any method by which a gene may be inserted into a cell, as described above. In a preferred embodiment, the plurality of human membrane genes are transfected in the first cell in a manner that allows these genes to be expressed and individually displayed on the cell surface. To achieve this, the optimized reverse transfection protocol described in the Examples section may be used. Alternatively, the expression and the individual display of the genes may be achieved by any known gene transfer technique including, but not limited to, retrovirus transduction, lentivirus transduction, lipofection and CRISPR.

The first cell in the solid support structure of the present invention can be any standard cell known in the art suitable for transfection and expression of a human membrane gene, for example, a human 293T cell. Alternatively, the first cell is a Chinese Hamster Ovary (CHO) cell. Another example of the first cell is a COS-7 cell. In preferred embodiments, the first cell is a human 293T.2A cell which expresses an immune-related adaptor. Examples of the immune-related adaptor include, but are not limited to DAP10, DAP12, FcRγ and CD3E. The second cell of the present invention is an immune cell whose activity is modulated upon interaction with proteins displayed on the first cell. In some embodiments, the second in the methods of the invention is an immune cell, for example, a T cell. Exemplary T cells include but not limited to Jurkat cells, naïve T cells, effector T cells, exhausted T cells, anergic T cells and regulatory T cells. Alternatively, the second cell may be a myeloid-derived suppressor cell.

In some embodiments, the second cell in the methods of the invention is engineered to stably express a cell assay sensor or detectable reporter, for example, a reporter gene expressing a fluorescent protein, or expressing an enzyme, so as to provide a cellular assay readout. In some embodiments, the reporter gene is contained in a construct comprising an inducible transcription control element driving the expression of the reporter gene. In some embodiments, the reporter construct is a cytotoxicity related reporter construct. In other embodiments, the reporter construct is an apoptosis related reporter construct. In yet another embodiments, the reporter construct is a proliferation related reporter construct.

The reporter gene used to detect the effect of a human membrane gene on the activity of the T cell can be generated by any standard methods known in the art. As describe above, a reporter gene construct is comprised of an inducible transcriptional control element driving the expression of the reporter gene, for example using a T cell related transcription responsive element for expression of a green fluorescent protein (GFP). Exemplary T cell related transcription responsive elements include, but are not limited to, NF-kB, NF-AT, AP-1, EGR2, MAPK and PI3K. Suitable reporters of the present invention include, but are not limited to, enzymes, fluorescent proteins, photo-proteins, fusion proteins and epitope tags. Examples of enzyme reporters include, but are not limited to, beta-galactosidase, alkaline phosphatase, beta-lactamase, luciferase and nitroreductase. Examples of fluorescent proteins include, but are not limited to, Aequorea victoria green fluorescent protein (GFP) and variants thereof (e.g., cyan fluorescent protein and yellow fluorescent protein). Suitable photo-proteins include, but are not limited to, aequorin. Alternatively, the reporter gene of the present invention is a cytokine gene. Exemplary cytokine include, but are not limited to, IFN-gamma, TNF-alpha and IL-10.

In the methods of the present invention, the first cell (e.g., an human 293T.2A cell which serves as an antigen presenting cell) is cultured with the second cell (e.g., a T cell). The term "culturing" refers to the in vitro propagation of cells or organisms on or in media of various kinds. It is understood that the descendants of a cell grown in culture may not be completely identical (e.g., morphologically, genetically, or phenotypically) to the parent cell. Cells are cultured under conditions (e.g., culture medium, temperature, oxygen, $CO_2$, incubation time) in which such cells can be maintained as viable cells and interact with other cells to activate signal transduction pathways. As such, the cells can be cultured in any suitable culture medium which contains components necessary for cell growth, such as carbon, nitrogen and micro-nutrients. Determination of suitable culture medium and growth conditions for such cells is well within the skill of the art.

The cells used in the methods of the invention may be cultured in a variety of media. Commercially available media such as Ham's F10™ (Sigma), Minimal Essential Medium™ (MEM), (Sigma), RPMI-1640 (Sigma), and Dulbecco's Modified Eagle's Medium™ (DMEM), (Sigma) are suitable for cell cultures. In addition, any of the media described in Ham et al., *Meth. Enz.* 58:44 (1979), Barnes et al., *Anal. Biochem.* 102:255 (1980), U.S. Pat. Nos. 4,767,704; 4,657,866; 4,927,762; 4,560,655; or 5,122,469; WO 90/03430; WO 87/00195; or U.S. Pat. No. Re. 30,985 may be used as culture media for cells, the entire teachings of which are incorporated herein by reference. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as gentamycin drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

IV. Screening Assays Using A Genome-Scale T Cell Activity Array (GS-TCAA)

The present invention also provides methods of identifying an immune modulator, which may have a potential therapeutic use in the treatment of autoimmune diseases and/or cancer. The methods involve providing the genome-scale T cell activity array (GS-TCAA) as described in Section II, allowing the expression of one of the plurality of human membrane genes in the first cell; co-culturing the first cell and the second cell; detecting the expression level of the reporter gene in the second cell; and comparing the expression level of the reporter gene with the expression level of the reporter gene in a control second cell wherein the control second cell is co-cultured with a control first cell that has not been transfected with one of the plurality of human membrane genes. An increase in the expression level of the reporter gene indicates that the displayed protein encoded by one of the plurality of human membrane genes acts as a stimulatory co-signaling molecule and stimulates the activity of the second cell line, and wherein a decrease in the expression level of the reporter gene indicates that the displayed protein encoded by one of the plurality of human membrane genes acts as an inhibitory co-signaling molecule and inhibits the activity of the second cell line.

An optimal T cell activation requires both antigen-specific primary signals through the TCR/CD3 complex and co-signaling involved in secondary signaling. In one embodiment, the immune modulator identified by the methods of the present invention regulates the immune system, in particular, the T cell activity. For example, the immune modulator may be a co-signaling molecule that regulates T cell activity. In some embodiments, the immune modulator activates T cell activity. In other embodiments, the immune modulator inhibits T cell activity. In yet other embodiments, the immune modulators may be used to treat autoimmune diseases and/or cancer.

In some embodiments, the immune modulator is selected from the group consisting of FOLH1, FAS, IL3RA, CD248, THBD, B7.1, GJB1, OX40L, 4-1BBL and B7.2, wherein the immune modulator increases or enhances T cell activity. Alternatively, the immune modulator is selected from the group consisting of FLT1, CXCR6, SEMA6a, RHCE, FCRLA, TNFRSF19, SEC22b, B3GNT1, NFAM1. LY6 and GP1BA, wherein the immune modulator exhibits an inhibitory effect on T cell activity. In some embodiments, the immune modulator is selected from the group consisting of FLT1, SEMA6a, SEC22b and GP1BA.

The present invention provides a broad cell-based screening approach that is suitable for use with many drug identification and discovery schemes, preferably in a high-throughput screening format. Automated high throughput screening is described, for example, in Burbaum et al., 1997, *Current Opinion in Chemical Biology,* 1:72-78; and Schullek et al., 1997, *Analyt. Biochem.* 246:20-29. In some embodiments, the methods of the invention are performed using robotics, for example, a robotic liquid handing system. As a non-limiting example, in high-throughput screening according to the present invention, liquid handling operations can be performed by a robotic Tecan Freedom EVO200 liquid handling platform. Other equipment needed for the screening (e.g., incubators, plate washers, plate handling systems, plate readers) can either be adapted for automated functioning, as necessary, or commercially purchased as automated modules. For example, movements of sample through the assay can be performed using the automatic plate handling system (Matrix PlateMate Plus, Thermo Scientific).

A "high throughput screen," as used herein, refers to an assay which provides for multiple candidate agents, samples or test compounds to be screened simultaneously. Examples of such assays may include the use of microtiter plates that are especially convenient because a large number of assays can be carried out simultaneously, using small amounts of reagents and samples. The methods of the present invention are easily carried out in a multi-well format including, but not limited to, 96-well, 384-well and 1536-well formats and are automated.

In some embodiments, the assays of the present invention are performed on cells using microscopic imaging to detect changes in spectral (e.g., fluorescent) properties. In other embodiments, the assays are performed in a multi-well format and spectral characteristics are determined using a microplate reader. Suitable devices for use in the methods of the invention are commercially available, for example, from Molecular Devices (FLEXstation™ microplate reader and fluid transfer system or FLIPR™ system), from Hamamatsu (FDSS 6000), PerkinElmer Life and Analytical Sciences (CellLux™), the "VIPR" voltage ion probe reader (Aurora, Bioscience Corp. Calif., USA) and InCell Imager (GE Healthcare Life Sciences). In some embodiments, the GFP detecting device for use in the methods of the invention is an InCell Imager. In other embodiments, the imaging analysis of the methods in the invention is performed using a Cellprolifer software.

Several commercial fluorescence imaging systems with integrated liquid handling are commercially available. These include but not limit to the Perkin Elmer CellLux-Cellular Fluorescence Workstation and the Hamamatsu FDSS6000 System. The excitation/emission characteristics differ for each fluorophore, therefore, the instruments are configured to detect the fluorophore chosen for each assay. Selection of appropriate fluorophore and configuration of the instruments to detect the fluorophore chosen for each experiment is within the skill of the artisan.

A configuration for cell imaging suitable for use in the methods of the present invention may involve the use of a microscope equipped with a computer system. The computer can include appropriate software for receiving user instructions, either in the form of user input into a set of parameter fields, or in the form of preprogrammed instructions, e.g., preprogrammed for a variety of different specific operations. The software optionally converts these instructions to appropriate language for controlling the operation of components of the system (e.g., for controlling a fluid handling element, robotic element and/or laser). The computer can also receive data from other components of the system, e.g., from a detector, and can interpret the data, provide it to a user in a human readable format, or use that data to initiate further operations, in accordance with any programming by the user. One example of such a configuration, ATTO's Attofluor™ RatioVision™ real-time digital fluorescence analyzer from Carl Zeiss, is a completely integrated work station for the analysis of fluorescent probes in living cells and prepared specimens (ATTO, Rockville, Md.).

After a potential therapeutic immune modulator is identified based on the methods and arrays of the invention, in vitro functional assays and in vivo mouse model analysis can be pursued for validation. In some embodiments, the methods of the invention comprise performing the genome-scale T cell activity array in combination with an assay selected from the group consisting of an in vitro functional assay, an in vivo assay, a receptor array assay, a bioinformatics assay, or a combination thereof.

An in vitro functional assay suitable for use in the methods of the invention includes any standard T cell assay known in the art, including, but not limited to proliferation assays, apoptosis assays or cytokine (e.g., IFN-g, IL-2 or IL-10) release assays. In some embodiments, the in vitro functional assay comprises culturing the second cell expressing one of the plurality of human membrane genes and the membrane-associated anti-CD3 antibody, or antigen-binding fragment thereof, with a primary T cell and performing the T cell assays. The primary T cell suitable for use in the methods of the invention includes any type of primary cells. Exemplary primary cells include, but are not limited to human primary CD8 cells or human primary CD4 cells.

The methods of the invention may be performed in combination with a Receptor Array Technology. The Receptor Array Technology is a well-established technology for screening counter-receptors of target proteins (Zhu Y et al, *Nat Commun*, 4: 2043, 2013; Yao S et al, *Immunity*, 34(5): 729-740, 2011). Briefly, the receptor array comprises a solid support structure comprising a plurality of wells wherein each of the plurality of wells comprises a cell that has been transfected with a gene encoding a receptor protein. A target gene (encoding a secreted protein) or the extracellular domain of the target gene (encoding a transmembrane protein, e.g., an immune modulator) is genetically fused to a tag gene (mouse IgG2a Fc, human IgG1 Fc, FLAG, or 6×HIS), to prepare fusion genes as described previously (Chapoval, A I. et al., *Mol Biotechnol* 21(3): 259-264, 2002). Upon transfection of individual fusion genes into 293T cells, the purified recombinant fusion protein is used to screen against the Receptor Array. A fluorescence-labeled secondary antibody against the tag is applied to detect the binding of the target protein, e.g., an immune modulator identified based on the methods of the present invention, to the transfected 293T cells and is screened using the Applied Biosystems 8200 Cellular Detection System and analyzed by CDS 8200 software. The entire contents of the foregoing references are incorporated herein by reference.

The therapeutic potential of the immune modulator identified by the methods of the invention can be further tested in vivo, e.g., in an animal model for an immune disease or cancer. In some embodiments, the in vivo assay comprises administering an immune modulator to an animal model for an autoimmune disease or cancer. An animal model for an autoimmune disease or cancer suitable for use in the methods of the invention includes any type of animal model for autoimmune disease or cancer known in the art, for example, a NOD-scid IL2Rgamma$^{null}$ mouse model injected with human melanoma cells and tumor-reactive T cells. In other embodiments, the animal model is a mouse model. Alternatively, the animal model is a rat model, a rabbit model, or a monkey model. In another embodiment, the animal model is a humanized mouse model, e.g., an immune-patient-derived xenograft (immune-PDX) model.

The methods of the invention may also be performed in combination with bioinformatic analysis. Bioinformatic approaches can be utilized to narrow down the genes associated with autoimmune diseases and cancers. Multiple stringent criteria are selected in order to identify genes that change significantly during the progression of disease and are potential signature genes for disease pathogenesis. In one embodiment, a ranking system is set up to identify specific genes that are only regulated in a specific autoimmune disease or cancer. Alternatively, genes that are common among different autoimmune diseases or cancers may be selected. To achieve this, the specific selection criteria described in the Examples section may be used.

V. Methods of Treatment

In one aspect, the present invention provides methods of treating an autoimmune disease or cancer in a subject in need thereof. The methods include administering to a subject in need thereof, an effective amount of an immune modulator identified by the screening methods of the present invention, as described above, thereby treating an autoimmune disease or cancer in the subject. In other embodiments, an effective amount of a regulator of an immune modulator identified by the screening methods of the present invention is administered to the subject in need thereof, thereby treating an autoimmune disease or cancer in the subject.

In some embodiment, the immune modulator is selected from the group consisting of FOLH1, FAS, IL3RA, CD248, THBD, B7.1, GJB1, OX40L, 4-1BBL and B7.2. In other embodiments, the immune modulator is selected from the group consisting of FLT1, CXCR6, SEMA6a, RHCE, FCRLA, TNFRSF19, SEC22b, B3GNT1, NFAM1. LY6 and GP1BA.

The regulator of an immune modulator suitable for use in the methods of the invention includes any agent that can regulate the expression and/or activity level of the immune modulator as described above. In some embodiments, the regulator of an immune modulator increases the expression level and/or the activity level of the immune regulator. In some embodiments, the regulator of an immune modulator decreases the expression level and/or the activity level of the immune regulator. In one embodiment, the regulator of an immune modulator binds to the immune modulator and either activates or inhibits its function. Exemplary regulators of an immune modulator include, but are not limited to, antibodies specific for the immune modulator, or antigen binding fragments thereof, small molecules specific for the immune modulator, and/or aptamers that specifically bind the immune modulator. In some embodiment, the regulator of an immune modulator may be used to treat autoimmune diseases and/or cancer.

The immune modulators identified based on the methods of the present invention, and/or regulators of the immune modulators can be administered by any suitable means, including parenteral administration (e.g., injection, infusion), and may be administered by subcutaneous, intraperitoneal, intrapulmonary, and intranasal, and, if desired for local treatment, intralesional administration. Parenteral infusions include intravenous, intraarterial, intraperitoneal, intramuscular, intradermal or subcutaneous administration. In addition, the immune modulators identified based on the methods of the present invention, and/or regulators of the immune modulators are suitably administered by pulse infusion, particularly with declining doses. The dosing can be given by injections, such as intravenous or subcutaneous injections. The route of administration can be selected according to various factors, such as whether the administration is brief or chronic. Other administration methods are contemplated, including topical, particularly transdermal, transmucosal, rectal, oral or local administration e.g. through a catheter placed close to the desired site. Injection, especially intravenous, is of interest.

In some embodiments, the methods comprise administering a therapeutically effective amount of an immune modulator as described herein to the subject. In some embodiments, the methods comprise administering a therapeutically effective amount of a regulator of an immune modulator to the subject. The therapeutically effective amount of an immune modulator or a regulator of an immune modulator is an amount sufficient to treat disease in a subject. The therapeutically effective dosage of immune modulators and/or regulators of immune modulators as described herein will vary somewhat from subject to subject, and will depend upon factors such as the age, weight, and condition of the subject and the route of delivery. Such dosages can be determined in accordance with procedures known to those skilled in the art.

Diseases that may be treated with the methods of the present invention include, but are not limited to, autoimmune diseases or cancer. "Treat" refers to any type of treatment that imparts a benefit to a patient, e.g., a patient afflicted with or at risk for developing a disease. Treating includes actions taken and actions refrained from being taken for the purpose of improving the condition of the patient (e.g., the relief of one or more symptoms), delay in the onset or progression of the disease.

As described herein, "autoimmune diseases" are those diseases that arise from an abnormal immune response of the body against substances and tissues normally present in the body, and include, but are not limited to, rheumatoid arthritis (RA), juvenile chronic arthritis (JCA), thyroiditis, graft versus host disease (GVHD), scleroderma, diabetes mellitus, Graves' disease, allergy, acute or chronic immune disease associated with an allogenic transplantation, such as, but not limited to, renal transplantation, cardiac transplantation, bone marrow transplantation, liver transplantation, pancreatic transplantation, small intestine transplantation, lung transplantation and skin transplantation.

As described herein, the term "cancer" refers to one of a group of diseases caused by the uncontrolled, abnormal growth of cells that can spread to adjoining tissues or other parts of the body. Cancer cells can form a solid tumor, in which the cancer cells are massed together, or exist as dispersed cells, as in leukemia. Types of cancer that are suitable to be treated by methods of the invention include, but are not limited to, adrenal cancer, anal cancer, bile duct cancer bladder cancer, bone cancer, brain/CNS tumors, breast cancer, castleman disease, cervical cancer colon/rectum cancer, endometrial cancer, esophagus cancer, eye cancer, gallbladder cancer, gastrointestinal cancer, kidney cancer, laryngeal and hypopharyngeal cancer, leukemia, liver cancer, lung cancer, lymphoma, lymphoma of the skin, malignant mesothelioma, multiple myeloma, myelodysplastic syndrome, nasal cavity and paranasal sinus cancer, nasopharyngeal cancer, neuroblastoma, non-hodgkin lymphoma, oral cavity and oropharyngeal cancer, osteosarcoma, ovarian cancer, pancreatic cancer, penile cancer, pituitary tumors, prostate cancer retinoblastoma, rhabdomyosarcoma, salivary gland cancer, skin cancer, small intestine cancer stomach cancer, testicular cancer, thymus cancer, thyroid cancer, uterine sarcoma, vaginal cancer, vulvar cancer, waldenstrom macroglobulinemia, and wilms tumor.

Pharmaceutical Formulations

Pharmaceutical formulations comprising immune modulators identified based on the methods of the present invention, and/or regulators of the immune modulators of the present invention may be prepared for storage by mixing the protein or nucleic acid having the desired degree of purity with optional physiologically acceptable carriers, excipients or stabilizers (Remington's Pharmaceutical Sciences 16th edition, Osol, A. Ed. (1980)), in the form of aqueous solutions, lyophilized or other dried formulations. Acceptable carriers, excipients, or stabilizers are nontoxic to recipients at the dosages and concentrations employed, and include buffers such as phosphate, citrate, histidine and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as Tween™, Pluronics™ or polyethylene glycol (PEG).

The formulations herein may also contain more than one active compound as necessary for the particular indication being treated. For example, if an autoimmune disease is to be treated, the formulations of the invention containing an immune modulator or a regulator of an immune regulator may be combined with drugs that are known to treat autoimmune diseases, such as methylprednisolone, kenalog, medrol, prednisolone, cortef, hydrocortisone, cortisone, triamcinolone acetonide, celestone soluspan, methylprednisolone acetate, orapred ODT, veripred 20, Solu-Medrol or methylprednisolone sodium. If cancer is to be treated, the formulations of the invention containing an immune modulator or a regulator of an immune regulator may be combined with drugs that are known to treat cancer, such as Abiraterone Acetate, ABITREXATE (Methotrexate), ABRAXANE (Paclitaxel Albumin-stabilized Nanoparticle Formulation), ADCETRIS (Brentuximab Vedotin), Ado-Trastuzumab Emtansine, ADRIAMYCIN (Doxorubicin Hydrochloride), ADRUCIL (Fluorouracil), Afatinib Dimaleate, AFINITOR (Everolimus), ALDARA (Imiquimod), Aldesleukin, Alemtuzumab, ALIMTA (Pemetrexed Disodium), ALOXI (Palonosetron Hydrochloride), AMBOCHLORIN (Chlorambucil), AMBOCLORIN (Chlorambucil), Aminolevulinic Acid, Anastrozole, Aprepitant, AREDIA (Pamidronate Disodium), ARIMIDEX (Anastrozole), AROMASIN (Exemestane), ARRANON (Nelarabine), Arsenic Trioxide, ARZERRA (Ofatumumab), Asparaginase Erwinia chrysanthemi, AVASTIN (Bevacizumab), Axitinib, Azacitidine, Bendamustine Hydrochloride, Bevacizumab, Bexarotene, BEXXAR (Tositumomab and I 131 Iodine Tositumomab), Bleomycin, Bortezomib, BOSULIF (Bosutinib), Cabazitaxel, Cabozantinib-S-Malate, CAMPATH (Alemtuzumab), CAMPTOSAR (Irinotecan Hydrochloride), Capecitabine, Carboplatin, Carfilzomib, CEENU (Lomustine), CERUBIDINE (Daunorubicin Hydrochloride), Cetuximab, Chlorambucil, Cisplatin, CLAFEN (Cyclophosphamide), Clofarabine, COMETRIQ (Cabozantinib-S-Malate), COSMEGEN (Dactinomycin), Crizotinib, Cyclophosphamide, CYFOS (Ifosfamide), Cytarabine, Dabrafenib, Dacarbazine, DACOGEN (Decitabine), Dactinomycin, Dasatinib, Daunorubicin Hydrochloride, Decitabine, Degarelix, Denileukin Diftitox, Denosumab, Dexrazoxane Hydrochloride, Docetaxel, Doxorubicin Hydrochloride, EFUDEX (Fluorouracil), ELITEK (Rasburicase), ELLENCE (Epirubicin Hydrochloride), ELOXATIN (Oxaliplatin), Eltrombopag Olamine, EMEND (Aprepitant), Enzalutamide, Epirubicin Hydrochloride, ERBITUX (Cetuximab), Eribulin Mesylate, ERIVEDGE (Vismodegib), Erlotinib Hydrochloride, ERWINAZE (Asparaginase Erwinia chrysanthemi), Etoposide, Everolimus, EVISTA (Raloxifene Hydrochloride), Exemestane, FARESTON (Toremifene), FASLODEX (Fulvestrant), FEMARA (Letrozole), Filgrastim, FLUDARA (Fludarabine Phosphate), Fludarabine Phosphate, FLUOROPLEX (Fluorouracil), Fluorouracil, Folinic acid, FOLOTYN (Pralatrexate), Fulvestrant, Gefitinib, Gemcitabine Hydrochloride, Gemtuzumab Ozogamicin, GEMZAR (Gemcitabine Hydrochloride), GILOTRIF (Afatinib Dimaleate), GLEEVEC (Imatinib Mesylate), HALAVEN (Eribulin Mesylate), HERCEPTIN (Trastuzumab), HYCAMTIN (Topotecan Hydrochloride), Ibritumomab Tiuxetan, ICLUSIG (Ponatinib Hydrochloride), Ifosfamide, Imatinib Mesylate, Imiquimod, INLYTA (Axitinib), INTRON A (Recombinant Interferon Alfa-2b), Iodine 131 Tositumomab and Tositumomab, Ipilimumab, IRESSA (Gefitinib), Irinotecan Hydrochloride, ISTODAX (Romidepsin), Ixabepilone, JAKAFI (Ruxolitinib Phosphate), JEVTANA (Cabazitaxel), Kadcyla (Ado-Trastuzumab Emtansine), KEOXIFENE (Raloxifene Hydrochloride), KEPIVANCE (Palifermin), KYPROLIS (Carfilzomib), Lapatinib Ditosylate, Lenalidomide, Letrozole, Leucovorin Calcium, Leuprolide Acetate, Lomustine, LUPRON (Leuprolide Acetate, MARQIBO (Vincristine Sulfate Liposome), MATULANE (Procarbazine Hydrochloride), Mechlorethamine Hydrochloride, MEGACE (Megestrol Acetate), Megestrol Acetate, MEKINIST (Trametinib), Mercaptopurine, Mesna, METHAZOLASTONE (Temozolomide), Methotrexate, Mitomycin, MOZOBIL (Plerixafor), MUSTARGEN (Mechlorethamine Hydrochloride), MUTAMYCIN (Mitomycin C), MYLOSAR (Azacitidine), MYLOTARG (Gemtuzumab Ozogamicin), Nanoparticle Paclitaxel (Paclitaxel Albumin-stabilized Nanoparticle Formulation), NAVELBINE (Vinorelbine Tartrate), Nelarabine, NEOSAR (Cyclophosphamide), NEUPOGEN (Filgrastim), NEXAVAR (Sorafenib Tosylate), Nilotinib, NOLVADEX (Tamoxifen Citrate), NPLATE (Romiplostim), Ofatumumab, Omacetaxine Mepesuccinate, ONCASPAR (Pegaspargase), ONTAK (Denileukin Diftitox), Oxaliplatin, Paclitaxel, Paclitaxel Albumin-stabilized Nanoparticle Formulation, Palifermin, Palonosetron Hydrochloride, Pamidronate Disodium, Panitumumab, Pazopanib Hydrochloride, Pegaspargase, Peginterferon Alfa-2b, PEG-INTRON (Peginterferon Alfa-2b), Pemetrexed Disodium, Pertuzumab, PLATINOL (Cisplatin), PLATINOL-AQ (Cisplatin), Plerixafor, Pomalidomide, POMALYST (Pomalidomide), Ponatinib Hydrochloride, Pralatrexate, Prednisone, Procarbazine Hydrochloride, PROLEUKIN (Aldesleukin), PROLIA (Denosumab), PROMACTA (Eltrombopag Olamine), PROVENGE (Sipuleucel-T), PURINETHOL (Mercaptopurine), Radium 223 Dichloride, Raloxifene Hydrochloride, Rasburicas, Recombinant Interferon Alfa-2b, Regorafenib, REVLIMID (Lenalidomide), RHEUMATREX (Methotrexate), Rituximab, Romidepsin, Romiplostim, RUBIDOMYCIN (Daunorubicin Hydrochloride), Ruxolitinib Phosphat, Sipuleucel-T, Sorafenib Tosylate, SPRYCEL (Dasatinib), STIVARGA (Regorafenib), Sunitinib Malate, SUTENT (Sunitinib Malate), SYLATRON (Peginterferon Alfa-2b), SYNOVIR (Thalidomide), SYNRIBO (Omacetaxine Mepesuccinate), TAFINLAR (Dabrafenib), Tamoxifen Citrate, TARABINE PFS (Cytarabine), TARCEVA (Erlotinib Hydrochloride), TARGRETIN (Bexarotene), TASIGNA (Nilotinib), TAXOL (Paclitaxel), TAXOTERE (Docetaxel), TEMODAR (Temozolomide), Temozolomide, Temsirolimus, Thalidomide, TOPOSAR (Etoposide), Topotecan Hydrochloride, Toremifene, TORISEL (Temsirolimus), Tositumomab and I 131 Iodine Tositumomab, TOTECT (Dexrazoxane Hydrochloride), Trametinib, Trastuzumab, TREANDA (Bendamustine Hydrochloride), TRISENOX (Arsenic Trioxide), TYKERB (Lapatinib Ditosylate), Vandetanib, VECTIBIX (Panitumumab), VeIP, VELBAN (Vinblastine Sulfate), VELCADE (Bortezomib), VELSAR (Vinblastine Sulfate), Vemurafenib, VEPESID (Etoposide), VIADUR (Leuprolide Acetate), VIDAZA (Azacitidine), Vinblastine Sulfate, Vincristine Sulfate, Vinorelbine Tartrate, Vismodegib, VORAXAZE (Glucarpidase), Vorinostat, VOTRIENT (Pazopanib Hydrochloride), WELLCOVORIN (Leucovorin Calcium), XALKORI (Crizotinib), XELODA (Capecitabine), XGEVA (Denosumab), XOFIGO (Radium 223 Dichloride), XTANDI (Enzalutamide), YERVOY (Ipilimumab), ZALTRAP (Ziv-Aflibercept), ZELBORAF (Vemurafenib), ZEVALIN (Ibritumomab Tiuxetan), ZINECARD (Dexrazoxane Hydrochloride), Ziv-Aflibercept, Zoledronic Acid, ZOLINZA (Vorinostat), ZOMETA (Zoledronic Acid), and ZYTIGA (Abiraterone Acetate).

The active ingredients may also be packaged in a microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

The formulations to be used for in vivo administration must be sterile. This is readily accomplished by filtration through sterile filtration membranes.

Generally, the ingredients of compositions are supplied either separately or mixed together in unit dosage form, for example, as a dry lyophilized powder or water free concentrate in a hermetically sealed container such as an ampoule or sachet indicating the quantity of active agent. Where the mode of administration is infusion, composition can be dispensed with an infusion bottle containing sterile pharmaceutical grade water or saline. Where the mode of administration is by injection, an ampoule of sterile water for injection or saline can be provided so that the ingredients may be mixed prior to administration. In an alternative embodiment, one or more of the pharmaceutical compositions of the invention is supplied in liquid form in a hermetically sealed container indicating the quantity and concentration of the agent.

The active agent can be incorporated into a pharmaceutical composition suitable for parenteral administration, typically prepared as an injectable solution. The injectable solution can be composed of either a liquid or lyophilized dosage form in a flint or amber vial, ampule or pre-filled syringe. The liquid or lyophilized dosage may further comprise a buffer (e.g., L-histidine, sodium succinate, sodium citrate, sodium phosphate or potassium phosphate, sodium chloride), a cryoprotectant (e.g., sucrose trehalose or lactose, a bulking agent (e.g., mannitol), a stabilizer (e.g., L-Methionine, glycine, arginine), an adjuvant (hyaluronidase).

The compositions of this invention may be in a variety of forms. These include, for example, liquid, semi-solid and solid dosage forms, such as liquid solutions (e.g., injectable and infusible solutions), microemulsion, dispersions, liposomes or suspensions, tablets, pills, powders, liposomes and suppositories. The preferred form depends on the intended mode of administration and therapeutic application. Typical modes of administration include parenteral (e.g., intravenous, subcutaneous, intraperitoneal, intramuscular) injection or oral administration.

Pharmaceutical compositions comprising an immune modulator or a regulator of an immune modulator described herein may be formulated for administration to a particular tissue. For example, in certain embodiments, it may be desirable to administer an immune modulator or a regulator of an immune modulator to connective tissue and/or tumor sites in a variety of organs.

In one embodiment, the therapeutic methods described herein are performed on a human. In a further embodiment, the methods described herein are not performed on a mouse or other non-human animal.

The present invention is further illustrated by the following examples, which are not intended to be limiting in any way. The entire contents of all references, patents and published patent applications cited throughout this application, as well as the Figures, are hereby incorporated herein by reference.

EXAMPLES

Example 1

Construction of the Genome-Scale T Cell Activity Array (GS-TCAA)

In order to conduct human genome-wide searches of targets for future immunotherapies, a genome-scale T cell activity array was developed. 6402 human membrane cDNA, covering 90% of the human membrane genome, were prepared using Qiagen miniprep kits, quantified and diluted for GS-TCAA construction.

Optimal T cell activation requires both antigen-specific primary signals through the TCR/CD3 complex, and co-signaling involved in secondary signaling. To set up functional T cell assays, a 293T cell based artificial antigen presenting cell line that stimulates basal T cell activation was designed, and fluoresent reporters were used as indicators of T cell activities (FIG. 1A). Specifically, the 293T.2A cells were used for the activity array. These 293T.2A cells were engineered 293T cells that express major immune-related adaptors (DAP10/DAP12/FcRγ/CD3E) for optimal expression of immune-related membrane genes. In addition, the 293T.2A cells were further engineered to express a membrane associated anti-CD3 antibody ScFv, which is a membrane form scfv of OKT-3 monoclonal antibody linked to a CD14 GPI anchor (FIG. 1B). These 293T.2A/m.anti-CD3 cells serve as both antigen presenting cells and cells expressing individual membrane genes.

Figure 2A:
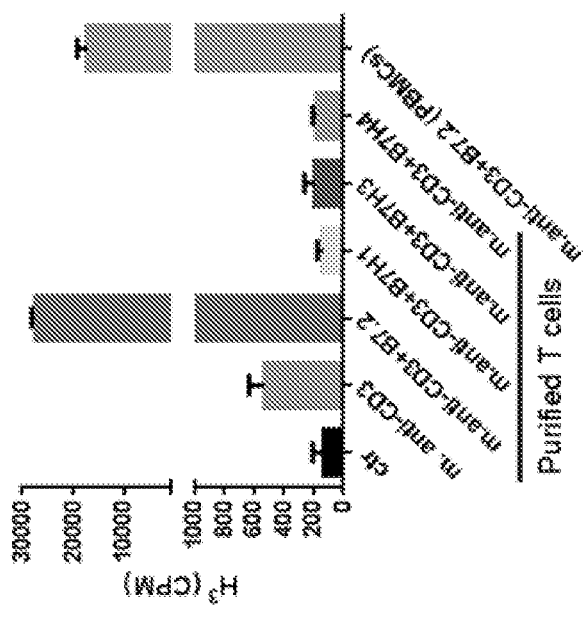
FIG. 2A depicts the efficacy of using 293T.2A cells transfected with the m.anti-CD3 construct and Jurkat cells expressing a GFP reporter for detecting membrane genes that are stimulatory on T cell activities. Briefly, 293T.2A cells were transient transfected with mock construct (ctr), the m.anti-CD3 plasmid with or without other T cell related membrane genes (e.g., B7.2, B7-H1, B7-H3 and B7-H4) and then co-cultured with purified human T cells or PBMCs. T cell proliferation indicated by thymidine corporation was shown 48 hours later.

Several constructs that contain T cell related transcription factor responsive elements (TFRE) (such as NF-kb, NF-AT, AP-1, or EGR2) that are under the control of a GFP reporter were designed for this assay and used as indicators of T cell activities (FIG. 1C). For example, a Jurkat cell line that stably expresses NF-KB-GFP was obtained. These cells did not generate visible GFP signal when co-cultured with 293T.2A cells. However, significant GFP signal was observed after co-culturing overnight with 293T.2A cells expressing a membrane anti-CD3 antibody and immune-related membrane genes (FIGS. 2A and 2B). In addition to Jurkat cell lines, primary immune cells, including naïve or effector T cells, exhausted, anergic T cells or Tregs were also included.

Read out for the activity array included proliferation related reporters, including cytokines (IFN-gamma, TNF-alpha or IL-10), and fluorescence-based signal-detection of T cell cytotoxicity or apoptosis. For the proliferation assay, the 293T.2A.m.anti-CD3 cells were irradiated (10,000 rad) right before T cell co-culture. About 72 hours later, 1 μl CCK-8 reagent (Dojindo) was loaded into each well the plates and followed by a 2-hour incubation before the absorbance reading at 450 nm by Envision plate reader (Perkin Elmer). For the cytotoxicity assay, 293T.2A.m.anti-CD3 stably expressing RFP was used. Briefly, gene plasmids in the GS-TCAA plates were reversely transfected into 293T.2A.m.anti-CD3 cells harboring RFP. 24 hours later, the plates were added with IncuCyte™ Kinetic Caspase-3/7 Apoptosis Assay Reagent (Essen Bioscience) plus OKT3 pre-activated or allo-PBMC activated human PBMCs. Both RFP and GFP signals at different time points after co-culture were detected by inCell analyzer (GE). For the T cell apoptosis assay, OKT3 pre-activated or allo-PBMC activated human PBMCs were labeled with cellTrace violet dye (Thermo Fisher) and mixed with IncuCyte™ Kinetic Caspase-3/7 Apoptosis Assay Reagent (Essen Bioscience) before loaded into the plates. Both RFP and GFP and Celltrace violet signals at different time points after co-culture were detected by inCell analyzer (GE). The T cell cytotoxicity were calculated by (% RFP+GFP+ cells/RFP+ cells), and the T cell apoptosis were calculated by (% Cell trace violet+ GFP+ cells/Cell trace violet+ cells).

Example 2

Detection and Screening of the Genome-Scale T Cell Activity Array

In order to optimize the screening system for the T cell activity array, the transfection efficiency of the 293T/m.anti-CD3 cells in 1536-well plates was tested and the optimal conditions required for T cell activities in these two cell co-culture systems were determined. In addition, GFP detection using an InCell Imaging system was also optimized for the activity array.

Gene clones were transferred into Greiner 1536-well imaging plates using an optimized protocol for the automatic plate handling system (Matrix PlateMate Plus, Thermo Scientific). Each GS-TCAA set contains four 1536-well imaging plates. For the array screening, an optimized reverse transfection protocol was utilized, such that these genes were individually displayed on the cell surface of 293T.2A/m.anti-CD3 cells. The cDNA library plasmids were mini-preped individually and then diluted in OptiMEM (4 μg/ml) and transferred into 384-deep-well plates (VWR), with 200 μl plasmids solution in each well. 2 μl of plasmid solution from four 384 plates containing various genes was transferred into each well of the low base 1536-well plates (Greiner) by a robotic liquid handling system (PlateMate, Thermo Scientific) to generate receptor array plates. The whole human membrane receptor array contains four 1536-well plates. Unless specified, these 1536-well plates were further foiled and stored in −80 degree for future experiments.

Figure 3:
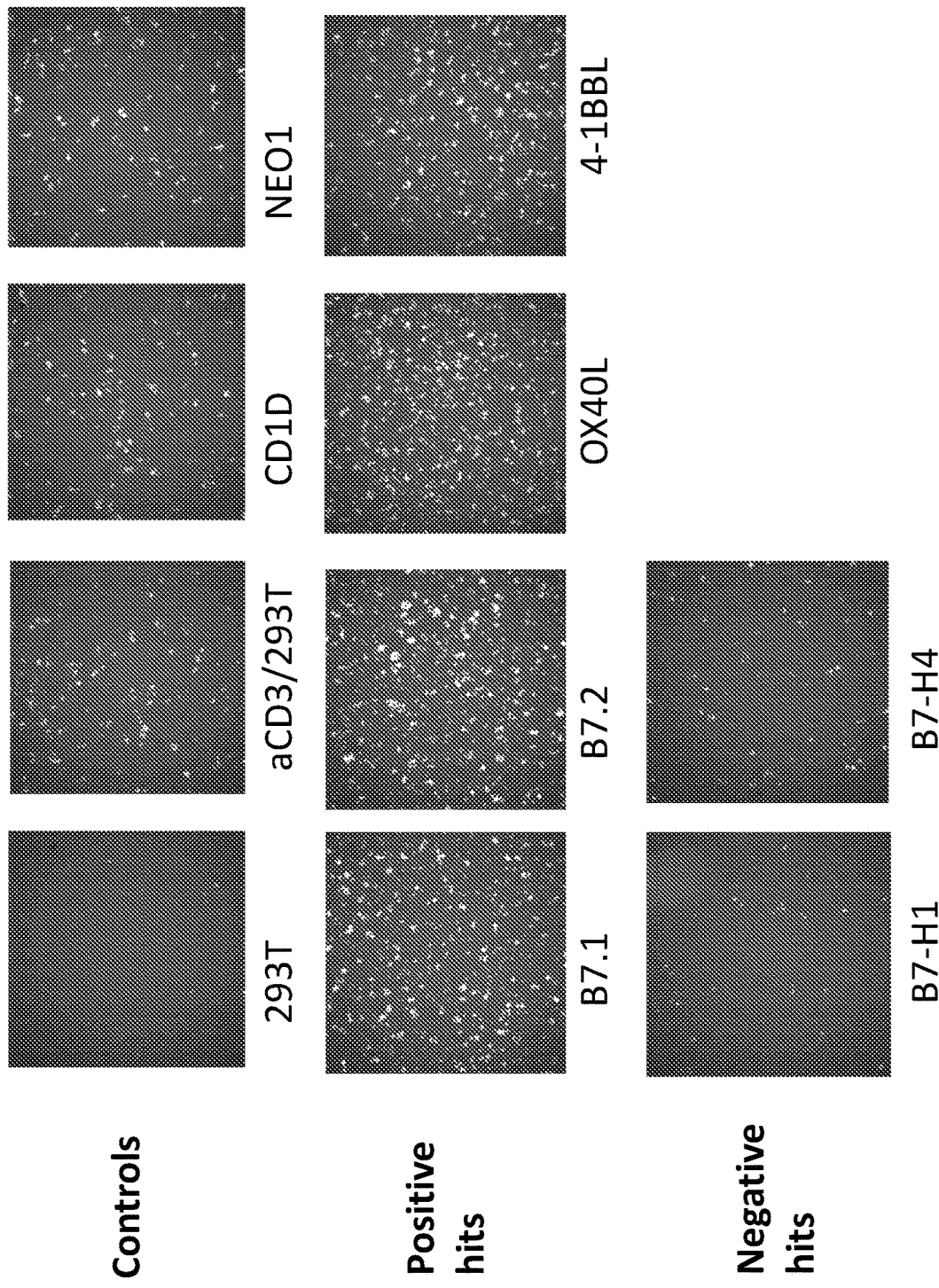
FIG. 3 is a series of images depicting membrane genes that were identified from GS-TCAA with either stimulatory or inhibitory function on T cell activity. Briefly, 293T.2A cells were transfected with mock construct (ctr), the m.anti-CD3 plasmid with or without other T cell related membrane genes and then co-cultured with Jurkat/NF-Kb GFP cells. GFP signal was detected 12 hours after co-culture. Data was obtained in 1536 imaging plates.

For Genome-scale T cell activity array setup, a set of human receptor array containing four 1536-well plates was brought out from −80 degree and put in incubator until the solution was completed thawed. The array plates were spin down (600 g, 2 min) and followed by reverse transfection. Briefly, 1536-well array plates were dispensed with 2 μl optiMEM containing lipofecamine 3000 (7 μl lipo/ml) with a robotic dispenser (Multidrop Combi, Thermo Scientific) per well and quickly shaked for 1 min by an ultra-speed orbital shaker. All plates were stored in room temperature for 20 min and followed by the addition of 293T.2A.m.anti-CD3 cells for T cell stimulation (2000 cells in 4 μl per well) by Multidrop. After that, the plates were further spin down (1000 g, 4 min) to get rid of the bubble inside each well before incubation at 37 degree. The T cell reporter cell or primary T cells (4000 cells), such as engineered Jurkat cell lines with different GFP reporters, were loaded into the array plates 24 hours after transfection. The plate imaging was performed 12 hours after co-culture of T cells with 293T based T cell stimulators by InCell image analyzer (GE). After optimal imaging analysis using Cellprofiler software, gene candidates with potential regulatory functions were identified. For example, if a molecule is not effective in modulating the T cell activity, the GFP signal will remain similar. If the molecule acts as an stimulatorgy signal for the T cell activity, then a relateively stronger GFP signal will be detected. Alternatively, if the molecule is inhibitory, a much weaker GFP signal will be observed. As demonstrated in FIG. 3, the 293T.2A/m.anti-CD3 cells alone stimulated T cell activation and generated detectable GFP signals that could serve as a basal signal. Expression of B7.1, B7.2, OX40L or 4-1BBL increased the fluorescence signal indicating that each of them served as a stimulatory signal for the T cell acitvity. In contrast, transfecting of the 293T.2A/m.anti-CD3 cells with B7-H1 or B7-H4 resulted in a decreased fluorescence signal, suggesting that these molecules inhibited the T cell activity.

Figure 4:
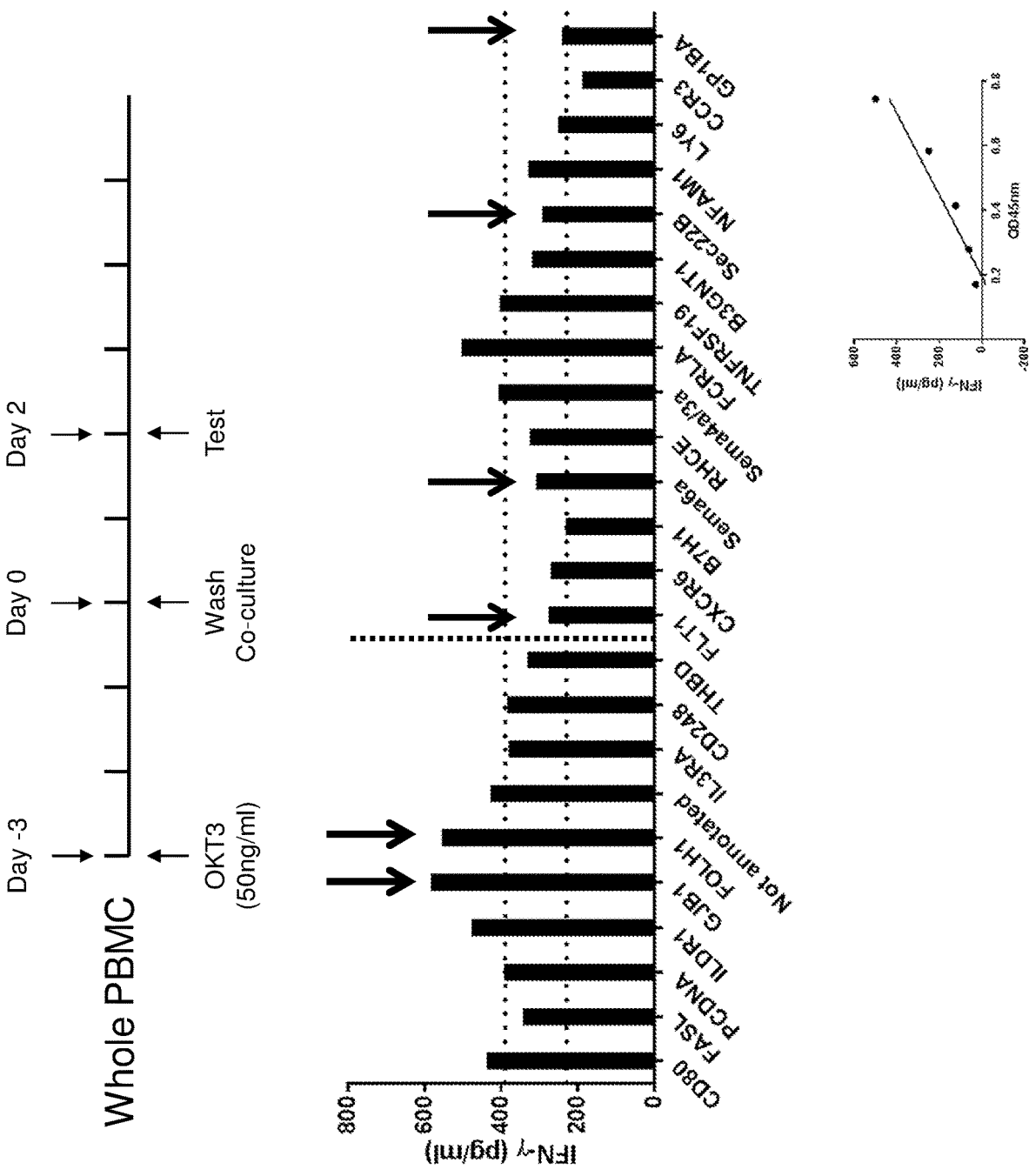
FIG. 4 depicts membrane genes that were identified from GS-TCAA with either stimulatory or inhibitory function on T cell activity. Briefly, 293T.2A cells were transfected with mock construct (ctr), the m.anti-CD3 plasmid with or without other T cell related membrane genes and then co-cultured with Jurkat. IFN-γ release was quantified.

Alternatively, the release of a specific cytokine may be used as a reporter and serve as an indicator of T cell activity. For cytokine detection, supernatant was collected 24 or 48 hours after co-culture and quantified by ELISA (eBoscience). As shown in FIG. 4, expression of GJB1 and FOLH1 stimulated the release of IFN-γ from the T cell, whereas expression of FLT1, SEMA6a, SEC22b and GP1BA reduced the IFN-γ release.

Figure 5:
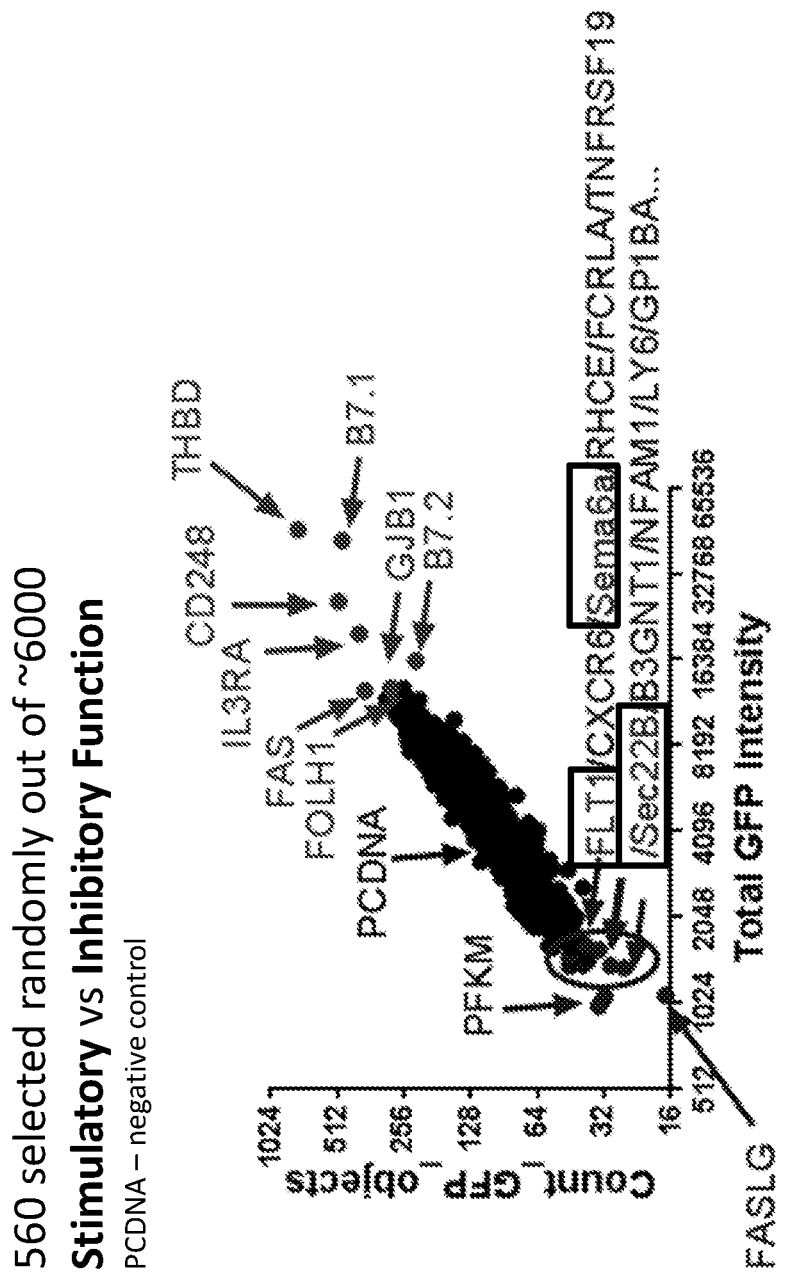
FIG. 5 is a graph depicting a representative analysis of the GS-TCAA hits. Cells transfected with membrane genes that have a stimulatory function on the T cell activity had a higher GFP reading than control, and cells transfected with membrane genes with an inhibitory function on T cell activities resulted in a lower GFP reading.
Figure 6:
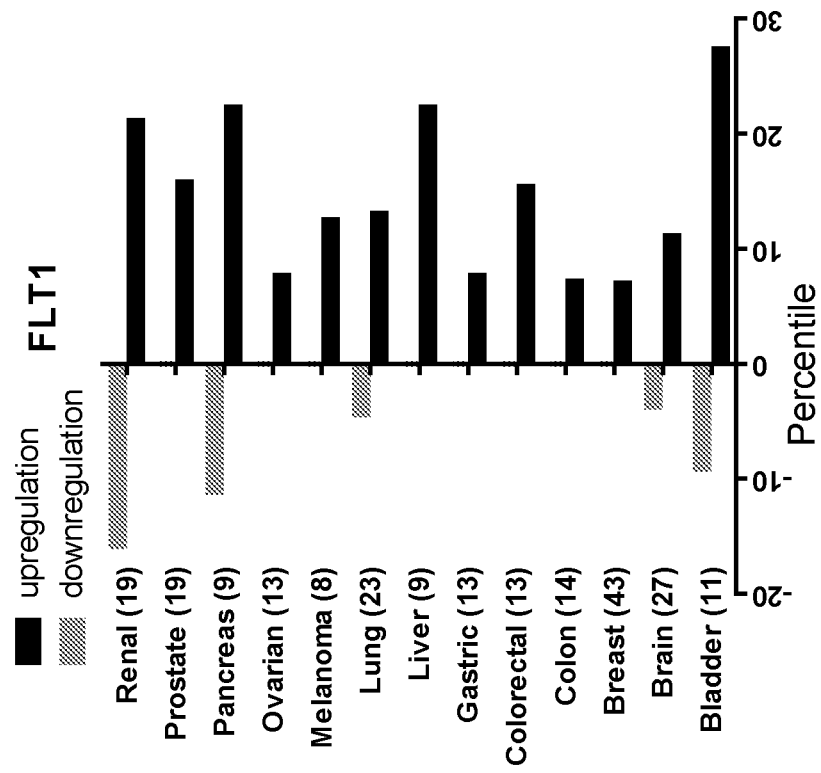
FIG. 6 is a graph depicting the differential expression of FLT1 in various types of cancer through analysis of Oncomine databases (Oncomine, Thermo Fisher).
Figure 7:
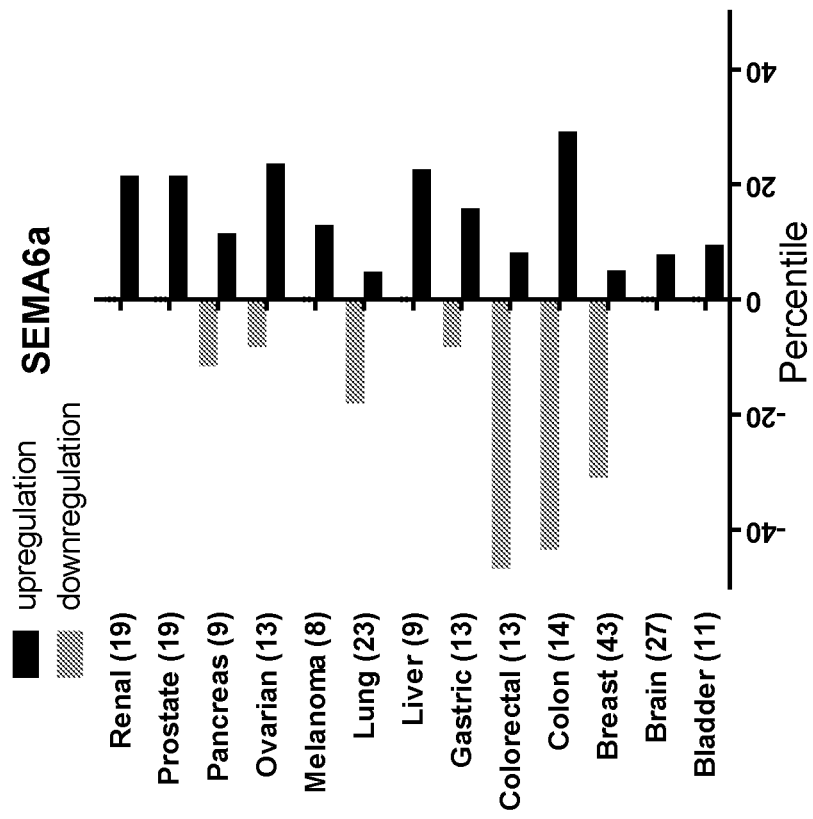
FIG. 7 is a graph depicting the differential expression of SEMA6a in various types of cancer through analysis of Oncomine databases (Oncomine, Thermo Fisher).

For the array screening, each T cell reporter cell was screened in triplicate plates and the average value of each gene was calculated and ranked, based on the density of GFP positive objects in the arrays. Cells transfected with membrane genes that have a stimulatory function on the Jurkat T cell activity would have a higher GFP reading than control, and cells transfected with membrane genes with an inhibitory function on T cell activities resulted in a lower GFP reading. All GFP signals were normalized and quantified with both GFP positive objects and total GFP density in each well by CellProfiler software (Broad Institute). As shown in FIG. 5, several genes with stimulatory and inhibitory function on the T cell activity were identified. The top candidates with inhibitory functions, e.g., FLT1, SEMA6a, SEC22b, and GP1Ba, from these GS-TCAA screenings were pooled together for further validation.

Example 3

Validation of Novel Immune Regulatory Genes with the Potential to Treat Cancer/Autoimmune Disease To further validate the function of gene candidates obtained from the GS-TCAA studies, in vitro functional assays with primary human T cells are performed. In addition, bioinformatics approaches are utilized to narrow down genes associated with autoimmune diseases and/or cancers. Several top gene candidates are also screened for potential counter-receptor identification in a receptor array system and are selected for in vivo studies to test the therapeutic potential of cancer/autoimmune disease in humanized mouse disease models, including the humanized mouse PDX models.

In Vitro T Cell Functional Assay

Top gene candidates identified from the GS-TCAA analysis are validated by in vitro functional assays using primary T cells. 293T.2A/m.anti-CD3 cells are transfected with gene candidates and co-cultured with human primary CD8 or CD4 cells. Assays for T cell proliferation, apoptosis, and release of cytokines (e.g., IFN-g, IL-2 or IL-10) are performed as described above.

Receptor Array Technology (RAT)

To screen unknown counter-receptors, a receptor array technology is performed as previously described (Zhu Y et al, *Nat Commun*, 4: 2043, 2013; Yao S et al, *Immunity*, 34(5): 729-740, 2011). Briefly, the target gene (encoding a secreted protein) or the extracellular domain of the target gene (encoding a transmembrane protein) is genetically fused to a tag gene (mouse IgG2a Fc, human IgG1 Fc, FLAG, or 6×HIS), to prepare fusion genes as described previously (Chapoval, A I. et al., *Mol Biotechnol* 21(3): 259-264, 2002). Upon transfection of individual fusion genes into 293T cells, the purified recombinant fusion protein is used to screen against the Receptor Array. A fluorescence-labeled secondary antibody against the tag is applied to detect the binding of the target protein to the transfected 293T cells and is screened using the Applied Biosystems 8200 Cellular Detection System and analyzed by CDS 8200 software.

The cell-based assay screens approximately 90% of all human membrane cDNAs which permits large scale screening using the Receptor Array Technology and screening of T cell-related surface-molecule interactions. A robust and stable system for cell-based high throughput screening was established, and the development of this innovative system for ultra-high throughput receptor-ligand screening was expanded using robotics and upgraded the Receptor Array from the original 384 well-plate format to a 1,536 well-plate format.

Utilizing the Tecan Freedom EVO 200 liquid handling platform for automation, a 4-5 fold decrease in the use of reagents and increased sensitivity was achieved when screening the 1,536-well plate format. The transfection procedures were optimized and demonstrated that high expression levels of the desired proteins were achieved by transfecting with a mixture of 5 ng of individual plasmid and Lipofectamine in the 1,536 well-plate format. Typically, 12 hours after transfection, 50-70% of the 293T cells in each well expressed the transfected plasmid. When new plasmids were incorporated into the system, quality control experiments were performed by examining their expression in randomly selected wells with specific monoclonal antibodies. This optimization and upgrade decreased the handling time and improved the overall screening by a 4-fold more efficient screening in timing, cost, and labor.

Therefore, by using the receptor array technology, interacting proteins for the gene candidates selected from the T cell activity array are identified. Identification of interacting proteins will provide additional insight about the immune function of the identified gene candidates and facilitate the selection of candidates for in vivo studies to test the therapeutic potential in mice tumor models.

In Vivo Mouse Model of Human Cancer

Antibodies specific for the top validated targets or recombinant proteins for the top candidates are generated in order to test their therapeutic potential in cancer models. 624 human melanoma (GP100+ HLA-A2+) cells and tumor-reactive T cells are injected into NOD-scid IL2Rgamma$^{null}$ mice. These mice receive several rounds of treatment with gene candidates and/or antibodies of the gene candidates, and tumor growth and the immune cell landscape or effector functions in the tumor sites are carefully monitored.

Patient-Derived Xenograft (PDX)

The heterogeneity of the tumor microenvironment (TME) is examined, in combination with immunohistochemistry (IHC), multiplex-immunofluorescence (multiplex-IF) and mass spectrometry (CyTOF) analysis in pre-treatment and on treatment tumor specimens collected from cancer patients. The combination of these technologies may be used as a tool to identify mechanistic interactions in the human TME. Specifically, differences in the immunological components of the TME are examined, and samples at baseline and at the moment of acquired resistance are compared. A humanized mouse model, known as an immune-patient-derived xenograft (immune-PDX) model, was developed and may be used in parallel with these analyses to study the human TME. These studies are imperative to uncover the mechanisms of response, resistance, and acquired resistance in the disease microenvironment, which eventually provide the basis for biomarker development and additional therapies based on the specific resistance mechanisms of the microenvironment.

Bioinformatic Approaches

Bioinformatic approaches are utilized to narrow down the genes associated with autoimmune diseases and cancers. Multiple stringent criteria are selected in order to identify genes that change significantly during the progression of disease and are potential signature genes for disease pathogenesis.

After the GS-TCAA and further function validation of potential gene candidates, a ranking system is set up to identify specific genes that are only regulated in a specific autoimmune disease or cancer. Alternatively, genes that are common among different autoimmune diseases or cancers may be selected.

For example, genes that encode only transmembrane and secreted proteins are selected, largely due to the ease for future manipulation of these molecules with therapeutic antibodies or recombinant proteins. In addition, this selection allows for the identification of counter-receptors and functions using a combination of the GS-TCAA and Receptor Array Technology. The second criterion is to select those genes that are shared with more than one disease. A ranking system is employed in which an up-regulated gene is scored with 1 point if it exists in each of the targeted diseases of interest. Higher numbers indicate that a gene is shared among different diseases. This reveals common mechanisms underlying different autoimmune diseases or cancer types.

Genes that are uniquely associated with a single disease are selected based on the selection criteria to identify genes that are specifically associated with one particular disease but not with other autoimmune diseases or cancer types. Subsequently, genes that are up-regulated or down-regulated in specific diseases with at least a two-fold change as the cutoff are selected. This is largely due to statistical considerations. A list of genes with specific protein domains that may be associated with specific immune functions are identified, for example, the Ig superfamily molecules. After initially identifying specific genes with these criteria, counter-receptor screening on these targets is performed using the Receptor Array Technology, and immune-related functional studies determine whether or not these molecules and their counter-receptors are potential targets for immune modulation.

Genes and proteins that are up-regulated in autoimmune diseases and in the cancer microenvironment are identified. Using major databases, such as NCBI, Oncomine, TCGA cancer database, Yale internal cancer databases and human protein Atlas, differentially expressed genes that are shared among various diseases are also identified. Subsequently, using Gene Set Enrichment Analysis (GSEA), genes that are related to the immune system, cytokine/chemokine signaling, or interferon signaling, and antigen presentation pathways, which play critical roles in the generation and progression of autoimmune disease and cancer, are identified. Finally, the up-regulated, shared disease genes are categorized by their subcellular location, and membrane proteins are focused on since they are more easily accessible to therapeutic agents. For certain genes, analysis is done to determine whether the transmembrane genes are members of the Immunoglobulin (Ig) superfamily, including FcR-like genes, HLA-related genes, and costimulatory molecules (CD86, B7-H1 aka CD274, and CTLA4,) which are known to affect autoimmune disease and cancer.

To identify the genes and proteins that are down-regulated in autoimmune diseases and in the cancer microenvironment, a similar approach is taken by using bioinformatics analyses of public and accessible databases to identify genes that are shared among various diseases.

Figure 8:
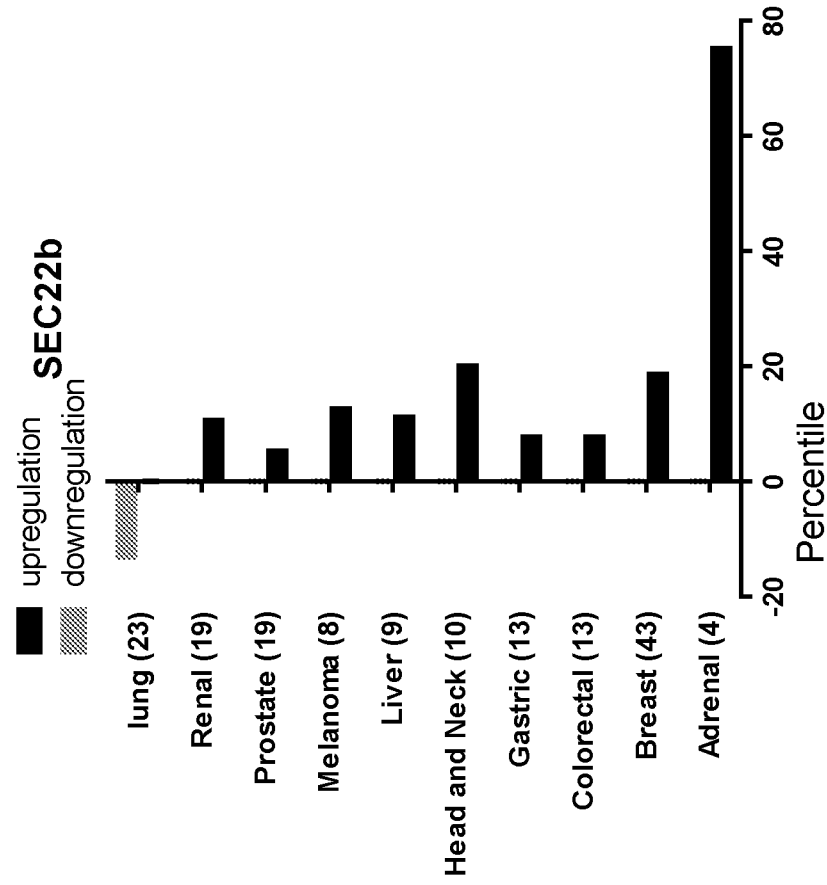
FIG. 8 is a graph depicting the differential expression of SEC22b in various types of cancer through analysis of Oncomine databases (Oncomine, Thermo Fisher).
Figure 9:
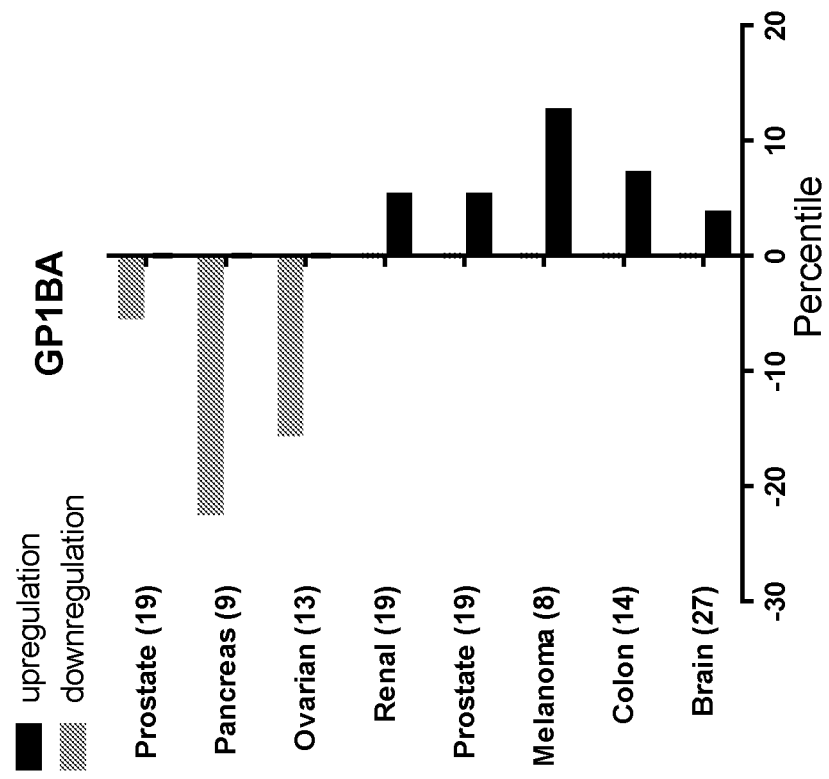
FIG. 9 is a graph depicting the differential expression of GP1BA in various types of cancer through analysis of Oncomine databases (Oncomine, Thermo Fisher).

Candidates with inhibitory functions on T cell activities identified from the GS-TCAA screenings, e.g., FLT1, SEMA6a, SEC22b, and GP1Ba, were further analyzed for their expression levels in various types of cancer. As demonstrated in FIGS. 6-9, expression levels of FLT1, SEMA6a, SEC22b, and GP1Ba were shown to be differentially regulated in different types of cancers. For example, expression of SEC22b was upregulated in a number of cancers such as renal cancer, prostate cancer, liver cancer, breast cancer, head and neck cancer, gastric cancer, colorectal cancer and adrenal cancer, whereas SEC22b was specifically downregulated in lung cancer (FIG. 8). This bioinformatics analysis further confirms the significance of the GS-TCAA in identifying immune modulators and suggests that these immune modulators may serve as potential therapeutic targets for treatment of cancer and/or autoimmune diseases.

EQUIVALENTS

Those skilled in the art will recognize, or be able to ascertain using no more than routine experimentation, many equivalents to the specific embodiments of the invention described herein. Such equivalents are intended to be encompassed by the following claims. The contents of all references, patents and published patent applications cited throughout this application are incorporated herein by reference.

We claim:

1. A Genome-Scale T Cell Activity Array (GS-TCAA), comprising
   a solid support structure comprising a plurality of wells wherein each of said plurality of wells comprises:
   a first cell that expresses a membrane associated anti-CD3 antibody, or antigen-binding fragment thereof, wherein said first cell has been transfected with a cDNA library encoding a plurality of human membrane genes in a manner that allows the display on said first cell of a protein encoded by one of said plurality of human membrane genes;
   a second cell that expresses a receptor on the cell surface and a reporter gene;
   wherein interaction between said receptor and said anti-CD3 antibody, or antigen-binding fragment thereof, provides a primary signal and stimulates the activity of said second cell line, and
   wherein an increase in the expression level of said reporter gene indicates that said displayed protein encoded by one of said plurality of human membrane genes acts as a stimulatory co-signaling molecule and stimulates the activity of said second cell line, and wherein a decrease in the expression level of said reporter gene indicates that said displayed protein encoded by one of said plurality of human membrane genes acts as an inhibitory co-signaling molecule and inhibits the activity of said second cell line.

2. The array of claim 1, wherein the solid support structure is a multi-well plate.

3. The array of claim 1, wherein the first cell is a human 293T cell; or a human 293T.2A cell which expresses an immune-related adaptor.

4. The array of claim 3, wherein the immune-related adaptor is selected from the group consisting of DAP10, DAP12, FcRγ and CD3E.

5. The array of claim 1, wherein the second cell is an immune cell.

6. The array of claim 5, wherein the immune cell is a myeloid-derived suppressor cell (MDSC); or the immune cell is a T cell.

7. The array of claim 1, wherein the reporter gene is contained in a DNA construct selected from the group consisting of a cytotoxicity related reporter construct, an apoptosis related reporter construct and a proliferation related reporter construct.

8. The array of claim 1, wherein said plurality of human membrane genes comprises a gene selected from a receptor gene, an immunoglobulin gene, a transporter gene and a signaling gene; said plurality of human membrane genes comprises about 1,000-7,000 genes; said plurality of human membrane genes comprises about 2,000-5,000 genes; or said plurality of human membrane genes comprises about 4,000-7,000 genes.

9. The array of claim 1, wherein said activity of said second cell is selected from the group consisting of cell proliferation, cell suppression, cell exhaustion, cell apoptosis, and cytokine release from cells.

10. A method of making a Genome-Scale T cell Activity Array (GS-TCAA), the method comprising:
    providing a solid support structure comprising a plurality of wells;
    culturing a first cell that expresses a membrane associated anti-CD3 antibody, or antigen-binding fragment thereof, into each of said plurality of wells;
    transfecting said first cell with a cDNA library encoding a plurality of human membrane genes in a manner that allows the display on said first cell of a protein encoded by one of said plurality of human membrane genes; and
    co-culturing a second cell that expresses a receptor on the cell surface and a reporter gene into each of said plurality of wells, thereby preparing a Genome-Scale T cell Activity Array,
    wherein interaction between said receptor and said anti-CD3 antibody, or antigen-binding fragment thereof, provides a primary signal and stimulates the activity of said second cell line, and
    wherein an increase in the expression level of said reporter gene indicates that said displayed protein encoded by one of said plurality of human membrane genes acts as a stimulatory co-signaling molecule and stimulates the activity of said second cell line, and wherein a decrease in the expression level of said reporter gene indicates that said displayed protein encoded by one of said plurality of human membrane genes acts as an inhibitory co-signaling molecule and inhibits the activity of said second cell line.

11. The method of claim 10, wherein the solid support structure is a multi-well plate.

12. The method of claim 10, wherein the first cell is a human 293T cell; or a human 293T.2A cell which expresses an immune-related adaptor.

13. The method of claim 10, wherein the second cell is an immune cell.

14. The array of claim 13, wherein the immune cell is a myeloid-derived suppressor cell (MDSC); or a T cell.

15. The method of claim 10, wherein the reporter gene is contained in a DNA construct selected from the group consisting of a cytotoxicity related reporter construct, an apoptosis related reporter construct and a proliferation related reporter construct.

16. A method of identifying an immune modulator, the method comprising:
    providing the Genome-Scale T cell Activity Array (GS-TCAA) of claim 1;
    allowing the expression of one of said plurality of human membrane genes in the first cell,
    co-culturing the first cell and the second cell;
    detecting the expression level of said reporter gene in the second cell; and
    comparing the expression level of said reporter gene with the expression level of said reporter gene in a control second cell wherein the control second cell is co-cultured with a control first cell that has not been transfected with one of said plurality of human membrane genes, wherein an increase in the expression level of said reporter gene indicates that said displayed protein encoded by one of said plurality of human membrane genes acts as a stimulatory co-signaling molecule and stimulates the activity of said second cell line, and wherein a decrease in the expression level of said reporter gene indicates that said displayed protein encoded by one of said plurality of human membrane genes acts as an inhibitory co-signaling molecule and inhibits the activity of said second cell line, thereby identifying said immune modulator.

17. The method of claim 16, wherein said immune modulator is selected from the group consisting of FOLH1, FAS, IL3RA, CD248, THBD, B7.1, GJB1, OX40L, 4-1BBL and B7.2; or said immune modulator is selected from the group consisting of FLT1, CXCR6, SEMA6a, RHCE, FCRLA, TNFRSF19, SEC22b, B3GNT1, NFAM1, LY6 and GP1BA; or said immune modulator is selected from the group consisting of FLT1, SEMA6a, SEC22b and GP1BA.

18. The method of claim 16, further comprising performing an assay selected from the group consisting of an in vitro functional assay, an in vivo assay, a receptor array assay, a bioinformatics assay, or a combination thereof.

19. The method of claim 18, wherein the in vitro functional assay comprises
culturing said second cell expressing one of said plurality of human membrane genes and the membrane-associated anti-CD3 antibody, or antigen-binding fragment thereof, with a primary T cell; and
performing an in vitro functional assay selected from the group consisting of a proliferation assay, an apoptosis assay and a cytokine release assay.

* * * * *